US006465614B1

United States Patent
Sanderson et al.

(10) Patent No.: US 6,465,614 B1
(45) Date of Patent: Oct. 15, 2002

(54) HIGH-AFFINITY RESPONSE-SELECTIVE C-TERMINAL ANALOGS OF C5A ANAPHYLATOXIN

(75) Inventors: Sam D. Sanderson; Simon A. Sherman; Leonid Kirnarsky, all of Omaha, NE (US); Stephen M. Taylor, Bellbird Park (AU)

(73) Assignee: The Board of Regents of the University of Nebraska, Omaha, NE (US)

( * ) Notice: Subject to any disclaimer, the term of this patent is extended or adjusted under 35 U.S.C. 154(b) by 0 days.

(21) Appl. No.: 09/358,020

(22) Filed: Jul. 21, 1999

Related U.S. Application Data

(63) Continuation of application No. 08/985,126, filed on Dec. 4, 1997, now Pat. No. 5,942,599, which is a continuation of application No. 08/299,285, filed on Aug. 31, 1994, now Pat. No. 5,696,230.

(51) Int. Cl.$^7$ .......................... A61K 38/00; C07K 5/00; C07K 7/00
(52) U.S. Cl. ...................... 530/328; 530/326; 530/325; 530/324; 530/327; 514/12; 514/13; 514/14; 514/15; 424/185.1
(58) Field of Search .................... 530/328, 327, 530/326, 325, 324; 514/12, 13, 14, 15; 424/185.1

(56) References Cited

U.S. PATENT DOCUMENTS

| 5,696,230 A | * 12/1997 | Sanderson et al. .......... 530/328 |
| 5,942,599 A | 8/1999 | Sanderson et al. |

OTHER PUBLICATIONS

Bernstein et al., J. Molec. Biol., 1977, 112: 535–542.
Bodammer et al., Int. Arch. Allergy, 1970, 39: 648–657.
Bothner-by et al., J. Amer. Chem. Soc., 1984, 106: 811.
Cheung et al., Can. J. Chem., 1977, 55: 906–910.
Dahiden et al., J. Immunol., 1979, 130: 857–862.
Drapeau et al., Biochem. Pharmacol., 1993, 45: 1289–1299.
Ember et al., J. Immunol., 1992, 148: 3165–3173.
English et al., J. Immunol. Meth., 1974, 5: 249–252.
Friedl et al., FASEB J., 1989, 3: 2512–2518.
Ember et al., Amer. J. Pathol., 1994, 144: 393–403.
Goodman et al., J. Immunol., 1982, 129: 70–75.
Haston et al., J. Immunol. Methods, 1985, 81: 229–237.
Hruby & Nikiforovich, Molecular Conformation and Biological Interaction, 1991, P. Blaram & S. Ramasehan, Eds., Indian Acad. of Sci., Bangalore, pp. 429–445.
Hugli & Morgan, 1984, Ch. 4 in Regulation of Leukocyte Function, R. Snyderman, ed., Plenum Publishing Corp., pp. 109–153.
Jancarik et al., J. Appl. Cryst., 1991, 24: 409–411.
Kahn et al., J. Amer. Chem. Soc., 1988, 110: 1638–1639.
Kawai et al., J. Med. Chem., 1992, 35: 220–223.
Kawai et al., J. Med. Chem., 1991, 34: 2068–2071.
Kemp et al., Tetra. Lett., 28: 4545–4648.
Kemp et al., Tetra. Lett., 29: 5057–5060.
Kohl et al., Eur. J. Immunol., 1993, 23: 646–652.
Marceau et al., Circ. Res., 1990, 67: 1059–1070.
Marion et al., Biochem. Biophys. Res. Commun., 1983, 113: 967.
Marshall, Can. J. Chem., 1973, 51: 1915–1919.
Mollison et al., Agents & Action, 1991, Suppl. 35: 17–21.
Mollison et al., Proc. Natl. Acad. Sci. USA, 1989, 86: 292–296.
Morgan et al., J. Immunol., 1992, 148: 3937–3942.
Olson et al., J. Amer. Chem. Soc., 112: 323–333.
Or et al., J. Med. Chem., 1992, 35: 402–406.
Otting et al., J. Mag. Reson., 1986, 66: 187.
Rivier et al., Peptides: Chemistry, Structure and Biology, 1990, ESCOM Publishers, Leiden, Netherlands (specifically, Kahn et al., pp. 498–500; Kemp et al., pp. 861–864; and Nicolaou et al., pp. 881–884.
Rollins et al., J. Biol. Chem., 1988, 263: 520–526.
Sanderson et al., Abstract presented at 13th American Peptide Symposium, Jun. 20–25, 1993.
Sanderson et al., J. Med. Chem., 1994, vol. 37, pp. 3171–3180 (Abstract published in Advance ACS Abstracts Aug. 15, 1994).
Siciliano et al., Proc. Natl. Acad. Sci., 1994, 91: 1214–1218.
Scholz et al., Clin. Immunol. Immunopathal., 1990, 51: 297–307.
Schroeder et al., J. Immunol., 1987, 139: 3474–3483.
Sherman et al., J. Mag. Reson., 1992, 96: 457–472.
Sherman et al., Prog. Biophys. Molec. Biol., 1993, 59: 285–339.
Stimler et al., J. Immunol., 1981, 126: 2258–2261.
Taylor et al., Clin. Exp. Phar. Physiol. Supp., 1993, 1:A.
Toth et al., Protein Science, 1994, 3: 1159–1168 (not in app).
Vlattas et al., J. Med. Chem., 1994, 37: 2783–2790 (not in app).
Ward, Am. J. Med., 1991, 91: (suppl. 3C) 89S–94S.
Wutrich, in NMR of Proteins and Nucleic Acids, John Wiley & Sons, New York, 1986, 162–175.
Zuiderweg et al., Biochem., 1989, 28: 172–185.

* cited by examiner

*Primary Examiner*—Christopher S. F. Low
(74) *Attorney, Agent, or Firm*—Senniger, Powers, Leavitt & Roedel

(57) ABSTRACT

High-affinity response-selective C-terminal analogs of C5a anaphylatoxin are provided. Whereas natural C5a has considerable flexibility in the C-terminal region, the analogs of the invention possess a backbone conformation which is constrained at the C-terminus to a β-turn. The stabilized β-turn confers a marked increase in potency of the analogs; the particular β-turn motif further confers the capability to selectively elicit certain biological responses associated with C5a. Exemplary compounds of the invention are decapeptide analogs of the formula: A1-Ser-Phe-Lys-A2-A3-A4-A5-A6-A7, with the constrained β-turn being localized in the region of A4–A7.

14 Claims, 7 Drawing Sheets

Figure 1:
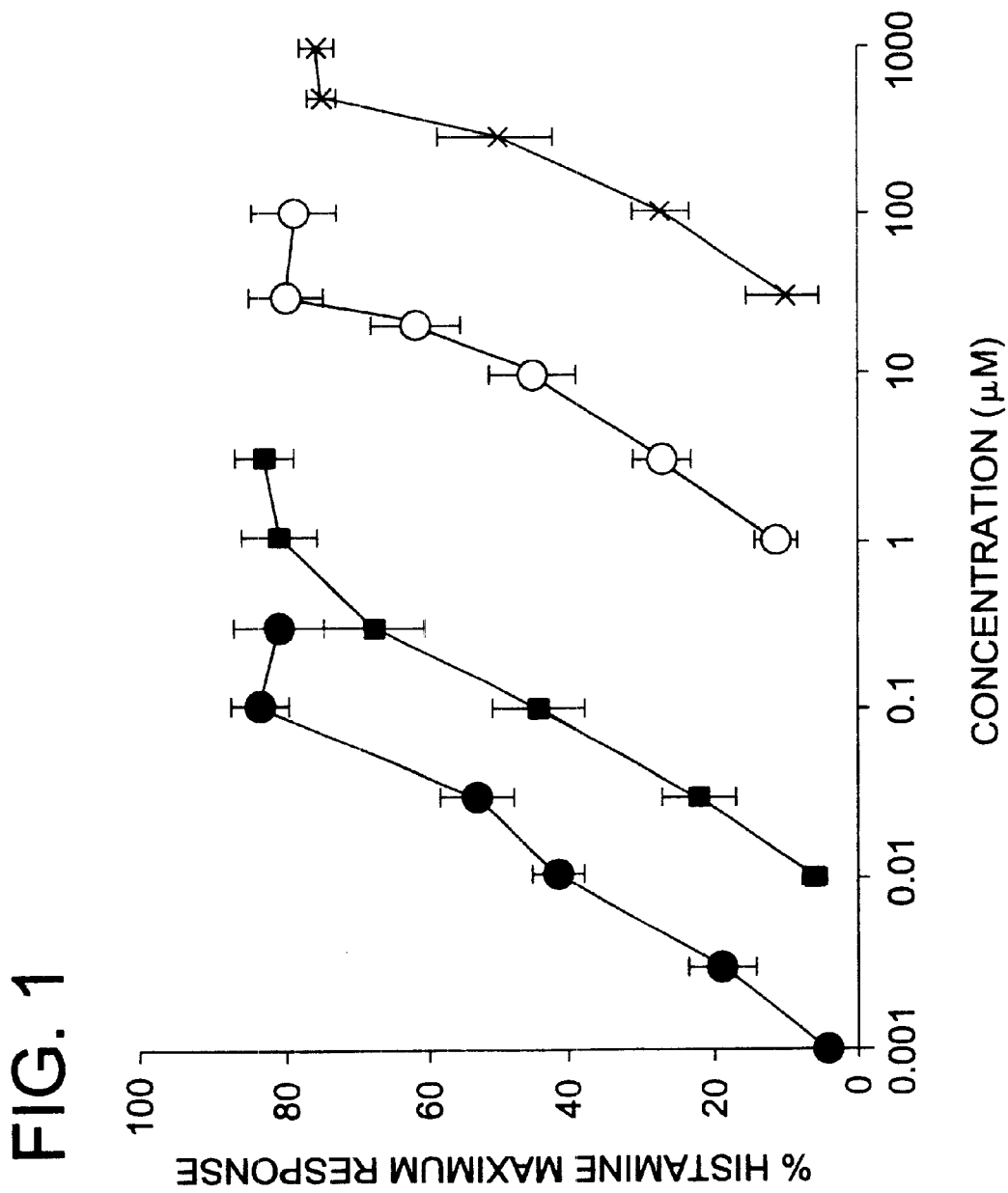

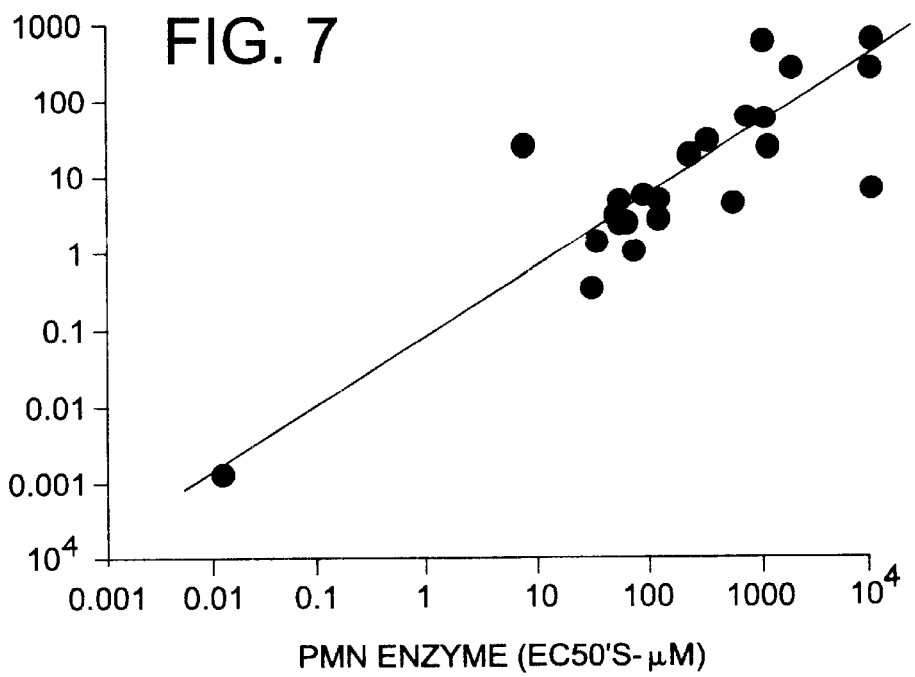
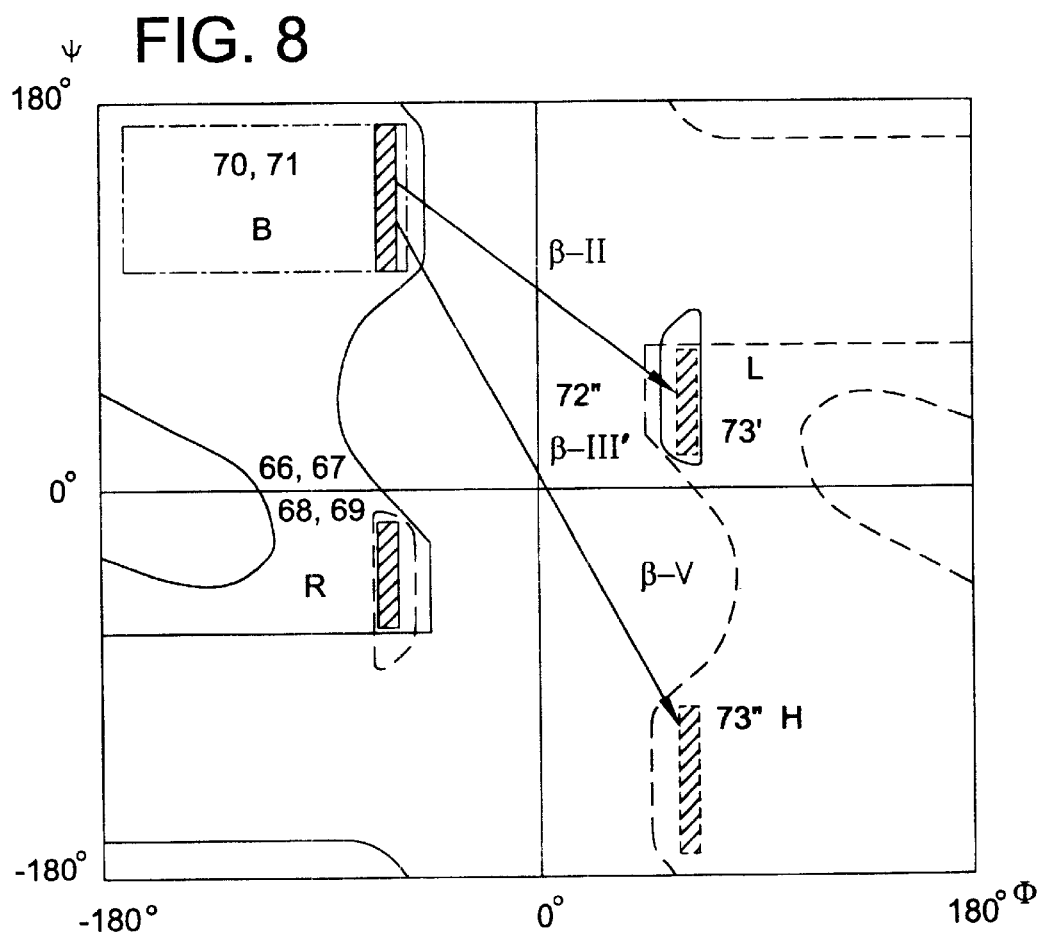

```
                         SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
         (A) LENGTH: 10 amino acids
         (B) TYPE: amino acid
         (C) STRANDEDNESS: Not Relevant
         (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 1:

Ile Ser Phe Lys Asp Met Gln Leu Gly Arg
1               5                   10

(2) INFORMATION FOR SEQ ID NO: 2:

(i) SEQUENCE CHARACTERISTICS:
         (A) LENGTH: 10 amino acids
         (B) TYPE: amino acid
         (C) STRANDEDNESS: Not Relevant
         (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 2:

Tyr Ser Phe Lys Asp Met Gln Leu Gly Arg
1               5                   10

(2) INFORMATION FOR SEQ ID NO: 3:

(i) SEQUENCE CHARACTERISTICS:
         (A) LENGTH: 10 amino acids
         (B) TYPE: amino acid
         (C) STRANDEDNESS: Not Relevant
         (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 3:

Tyr Ser Phe Lys Asp Met Gln Leu Pro Arg
1               5                   10

(2) INFORMATION FOR SEQ ID NO: 4:
```

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 4:

Tyr Ser Phe Lys Asp Met Gln Pro Gly Arg
1               5                   10

(2) INFORMATION FOR SEQ ID NO: 5:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 5:

Tyr Ser Phe Lys Asp Met Pro Leu Gly Arg
1               5                   10

(2) INFORMATION FOR SEQ ID NO: 6:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 6:

Tyr Ser Phe Lys Asp Met Pro Pro Gly Arg
1               5                   10

(2) INFORMATION FOR SEQ ID NO: 7:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 7:

Tyr Ser Phe Lys Asp Met Pro Leu Ala Arg
1               5                   10

(2) INFORMATION FOR SEQ ID NO: 8:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
            (A) NAME/KEY: Modified-site
            (B) LOCATION: 9
            (D) OTHER INFORMATION: "D-Alanine at position 9"

(xi) SEQUENCE DESCRIPTION: SEQ ID NO: 8:

Tyr Ser Phe Lys Asp Met Gln Leu Ala Arg
1               5                   10

(2) INFORMATION FOR SEQ ID NO: 9:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 9:

Tyr Ser Phe Lys Asp Met Gln Ile Gly Arg
1               5                   10

(2) INFORMATION FOR SEQ ID NO: 10:

(i) SEQUENCE CHARACTERISTICS:
            (A) LENGTH: 10 amino acids
            (B) TYPE: amino acid
            (C) STRANDEDNESS: single
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
            (A) NAME/KEY: Modified-site
            (B) LOCATION: 9
            (D) OTHER INFORMATION: "D-Alanine at position 9"

(xi) SEQUENCE DESCRIPTION: SEQ ID NO: 10:

Tyr Ser Phe Lys Asp Met Pro Leu Ala Arg
1               5                   10

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 11:

Tyr Ser Phe Lys Asp Met Pro Ala Gly Arg
1               5                   10

(2) INFORMATION FOR SEQ ID NO: 12:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Modified-site
        (B) LOCATION: 9
        (D) OTHER INFORMATION: "D-Alanine at position 9"

(xi) SEQUENCE DESCRIPTION: SEQ ID NO: 12:

Tyr Ser Phe Lys Asp Met Pro Ala Ala Arg
1               5                   10

(2) INFORMATION FOR SEQ ID NO: 13:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Modified-site
        (B) LOCATION: 9
        (D) OTHER INFORMATION: "D-Phenylalanine at
            position 9"

(xi) SEQUENCE DESCRIPTION: SEQ ID NO: 13:

Tyr Ser Phe Lys Asp Met Pro Leu Phe Arg

```
1               5                   10
```

(2) INFORMATION FOR SEQ ID NO: 14:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Modified-site
        (B) LOCATION: 9
        (D) OTHER INFORMATION: "D-Proline at position 9"

(xi) SEQUENCE DESCRIPTION: SEQ ID NO: 14:

```
Tyr Ser Phe Lys Asp Met Pro Leu Pro Arg
1               5                   10
```

(2) INFORMATION FOR SEQ ID NO: 15:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 15:

```
Tyr Ser Phe Lys Asp Ala Pro Leu Gly Arg
1               5                   10
```

(2) INFORMATION FOR SEQ ID NO: 16:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 16:

```
Tyr Ser Phe Lys Asp Cys Pro Leu Gly Arg
1               5                   10
```

(2) INFORMATION FOR SEQ ID NO: 17:

(i) SEQUENCE CHARACTERISTICS:
        (A) LENGTH: 10 amino acids
        (B) TYPE: amino acid (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 17:

Tyr Ser Phe Lys Asp Cys Pro Leu Cys Arg
1               5                   10

(2) INFORMATION FOR SEQ ID NO: 18:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 18:

Tyr Ser Phe Lys Asp Cys Pro Leu Cys Arg
1               5                   10

(2) INFORMATION FOR SEQ ID NO: 19:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
            (A) NAME/KEY: Modified-site
            (B) LOCATION: 9
            (D) OTHER INFORMATION: "D-Alanine at position 9"

(xi) SEQUENCE DESCRIPTION: SEQ ID NO: 19:

Tyr Ser Phe Lys Asp Ala Pro Leu Ala Arg
1               5                   10

(2) INFORMATION FOR SEQ ID NO: 20:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 20:

Tyr Ser Phe Lys Gly Met Leu Leu Gly Arg
1               5                   10

(2) INFORMATION FOR SEQ ID NO: 21:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 21:

Tyr Ser Phe Lys Gly Leu Leu Leu Gly Arg
1               5                   10

(2) INFORMATION FOR SEQ ID NO: 22:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
            (A) NAME/KEY: Modified-site
            (B) LOCATION: 10
            (D) OTHER INFORMATION: "D-Arginine at position 10"

(xi) SEQUENCE DESCRIPTION: SEQ ID NO: 22:

Tyr Ser Phe Lys Gly Met Leu Leu Gly Arg
1               5                   10

(2) INFORMATION FOR SEQ ID NO: 23:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO: 23:

Tyr Ser Phe Lys Gly Met Pro Leu Gly Arg
1               5                   10

(2) INFORMATION FOR SEQ ID NO: 24:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Modified-site
        (B) LOCATION: 9
        (D) OTHER INFORMATION: "D-Alanine at position 9"

(xi) SEQUENCE DESCRIPTION: SEQ ID NO: 24:

```
Tyr Ser Phe Lys Pro Met Gln Leu Ala Arg
1               5                   10
```

(2) INFORMATION FOR SEQ ID NO: 25:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Modified-site
        (B) LOCATION: 9
        (D) OTHER INFORMATION: "Aib at position 9"

(xi) SEQUENCE DESCRIPTION: SEQ ID NO: 25:

```
Tyr Ser Phe Lys Asp Met Gln Leu Xaa Arg
1               5                   10
```

(2) INFORMATION FOR SEQ ID NO: 26:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Modified-site
        (B) LOCATION: 9..10
        (D) OTHER INFORMATION: "D-Alanine at position 9;
            N-methylated Arginine at position 10"

(xi) SEQUENCE DESCRIPTION: SEQ ID NO: 26:

```
Tyr Ser Phe Lys Asp Met Gln Leu Ala Arg
1               5                   10

(2) INFORMATION FOR SEQ ID NO: 27:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Modified-site
        (B) LOCATION: 8..9
        (D) OTHER INFORMATION:  "'-Methylated Leucine at
            position 8; D-Alanine at position 9"

(xi) SEQUENCE DESCRIPTION: SEQ ID NO: 27:

Tyr Ser Phe Lys Asp Met Gln Leu Ala Arg
1               5                   10

(2) INFORMATION FOR SEQ ID NO: 28:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Modified-site
        (B) LOCATION: 9..10
        (D) OTHER INFORMATION: "D-Alanine at position 9;
            N-methylated Arginine at position 10"

(xi) SEQUENCE DESCRIPTION: SEQ ID NO: 28:

Tyr Ser Phe Lys Asp Met Gln Leu Ala Arg
1               5                   10

(2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Modified-site
        (B) LOCATION: 8
```

(D) OTHER INFORMATION: "N-Methylated, D-Alanine at
               position 9"

(xi) SEQUENCE DESCRIPTION: SEQ ID NO: 29:

Tyr Ser Phe Lys Asp Met Gln Leu Ala Arg
1               5                   10

(2) INFORMATION FOR SEQ ID NO: 30:

(i) SEQUENCE CHARACTERISTICS:
          (A) LENGTH: 10 amino acids
          (B) TYPE: amino acid
          (C) STRANDEDNESS: Not Relevant
          (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
          (A) NAME/KEY: Modified-site
          (B) LOCATION: 8..9
          (D) OTHER INFORMATION: "N-Methylated Leucine at
               position 8; D-Alanine at position 9"

(xi) SEQUENCE DESCRIPTION: SEQ ID NO: 30:

Tyr Ser Phe Lys Asp Met Gln Leu Ala Arg
1               5                   10

(2) INFORMATION FOR SEQ ID NO: 31:

(i) SEQUENCE CHARACTERISTICS:
          (A) LENGTH: 10 amino acids
          (B) TYPE: amino acid
          (C) STRANDEDNESS: Not Relevant
          (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
          (A) NAME/KEY: Modified-site
          (B) LOCATION: 7..9
          (D) OTHER INFORMATION: "N-Methylated Glutamine at
               position 7; D-Alanine at position 9"

(xi) SEQUENCE DESCRIPTION: SEQ ID NO: 31:

Tyr Ser Phe Lys Asp Met Gln Leu Ala Arg
1               5                   10

(2) INFORMATION FOR SEQ ID NO: 32:

(i) SEQUENCE CHARACTERISTICS:
          (A) LENGTH: 10 amino acids
          (B) TYPE: amino acid
          (C) STRANDEDNESS: Not Relevant
          (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
            (A) NAME/KEY: Modified-site
            (B) LOCATION: 9..10
            (D) OTHER INFORMATION: "N-Methylated D-Alanine at
                position 9; N-Methylated Arginine at position 10"

(xi) SEQUENCE DESCRIPTION: SEQ ID NO: 32:

Tyr Ser Phe Lys Asp Met Gln Leu Ala Arg
1               5                   10

(2) INFORMATION FOR SEQ ID NO: 33:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
            (A) NAME/KEY: Modified-site
            (B) LOCATION: 8..10
            (D) OTHER INFORMATION: "N-Methylated Leucine at
                position 8; D-Alanine at position 9:  N-Methylated
                Arginine at position 10"

(xi) SEQUENCE DESCRIPTION: SEQ ID NO: 33:

Tyr Ser Phe Lys Asp Met Gln Leu Ala Arg
1               5                   10

(2) INFORMATION FOR SEQ ID NO: 34:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
            (A) NAME/KEY: Modified-site
            (B) LOCATION: 7..10
            (D) OTHER INFORMATION: "N-Methylated Glutamine at
                position 7; D-Alanine at position 9; N-Methylated
                Arginine at position 10"

(xi) SEQUENCE DESCRIPTION: SEQ ID NO: 34:

Tyr Ser Phe Lys Asp Met Gln Leu Ala Arg
1               5                   10

(2) INFORMATION FOR SEQ ID NO: 35:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
             (A) NAME/KEY: Modified-site
             (B) LOCATION: 7..9
             (D) OTHER INFORMATION: "N-Methylated Glutamine at
                  position 7; N-Methylated Leucine at position 8;
                  D-Alanine at position 9"

(xi) SEQUENCE DESCRIPTION: SEQ ID NO: 35:

Tyr Ser Phe Lys Asp Met Gln Leu Ala Arg
1               5                   10

(2) INFORMATION FOR SEQ ID NO: 36:

(i) SEQUENCE CHARACTERISTICS:
             (A) LENGTH: 10 amino acids
             (B) TYPE: amino acid
             (C) STRANDEDNESS: Not Relevant
             (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
             (A) NAME/KEY: Modified-site
             (B) LOCATION: 8..9
             (D) OTHER INFORMATION: "N-Methylated Leucine at
                  position 8; N-Methylated D-Alanine at position 9"

(xi) SEQUENCE DESCRIPTION: SEQ ID NO: 36:

Tyr Ser Phe Lys Asp Met Gln Leu Ala Arg
1               5                   10

(2) INFORMATION FOR SEQ ID NO: 37:

(i) SEQUENCE CHARACTERISTICS:
             (A) LENGTH: 10 amino acids
             (B) TYPE: amino acid
             (C) STRANDEDNESS: Not Relevant
             (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
             (A) NAME/KEY: Modified-site
             (B) LOCATION: 8..10
             (D) OTHER INFORMATION: "N-Methylated Leucine at
                  position 8; N-Methylated D-Alanine at position 9;
                  N-Methylated Arginine at position 10"

(xi) SEQUENCE DESCRIPTION: SEQ ID NO: 37:

Tyr Ser Phe Lys Asp Met Gln Leu Ala Arg
1               5                   10

HIGH-AFFINITY RESPONSE-SELECTIVE C-TERMINAL ANALOGS OF C5A ANAPHYLATOXIN

This application is a continuation of U.S. application Ser. No. 08/985,126, filed Dec. 4, 1997, issued Aug. 24, 1999 as U.S. Pat. No. 5,942,599, which is a continuation of U.S. application Ser. No. 08/299,285, filed Aug. 31, 1994, issued Dec. 9, 1997 as U.S. Pat. No. 5,696,230, the entireties of which are incorporated by reference herein.

FIELD OF THE INVENTION

This invention relates to the function and regulation of complement-derived anaphylatoxins in the body. In particular, this invention provides a series of high-affinity/high-potency C-terminal analogs of C5a anaphylatoxin, capable of eliciting selected biological responses associated with C5a. This invention further provides methods of using these analogs either (1) as agonists to induce specific desired biological responses associated with C5a, or (2) as high affinity templates for development of antagonists to inhibit specific undesired biological responses associated with C5a.

BACKGROUND OF THE INVENTION

The blood complement (C) plays an important role in host defense to foreign substances. Individuals that are deficient in certain C components often suffer recurrent and sometimes fatal infections. Activation of the C system results in the production of the anaphylatoxins, C3a and C5a. These fragments are biologically active cleavage products of the larger C proteins C3 and C5, respectively. C5a is a short (74 residues in human) glycoprotein that is generated by enzymatic cleavage of C5.

C5a is recognized as a principal mediator of local and systemic inflammatory responses because of its ability to activate and recruit neutrophils, induce spasmogenesis, increase vascular permeability and stimulate the release of secondary inflammatory mediators from a variety of cell types (e.g., leukocytes and macrophages). C5a also appears to play a role in the modulation of immune response because of its ability to induce, directly or indirectly, the synthesis and release of the cytokines interleukin-1 (IL-1), interleukin-6 (IL-6), interleukin-8 (IL-8), and tumor necrosis factor-$\alpha$ (TNF-$\alpha$) from human monocytes. These inflammatory and immunomodulatory activities are believed to be expressed via a transmembrane, G-protein-mediated signal transduction mechanism when the C5a ligand interacts with its receptor(s) expressed on the surface of certain circulating and tissue cell types.

The proinflammatory activities of C5a may be classified into two broad categories. The first category of activity is generally associated with the release of histamines and other secondary mediators (e.g., vasoconstrictor and vasodilator eicosanoids). These activities of C5a affect many systems, and are associated with the phenomena of spasmogenesis and certain cell aggregatory activities (e.g., platelet aggregation). The second category of activity involves recruitment and activation of neutrophils and subsequent effects of such neutrophil accumulation and activation, such as increased vascular permeability, release of cytokines and other pro-inflammatory responses. The in vivo pharmacology of these two broad classes of C5a activities is described briefly by Drapeau et al. (1993), Biochem. Pharmacol., 45: 1289–1299. The regulation of neutrophils and other leukocytes by C5a has been reviewed by Hugli & Morgan (1984), Chapter 4 in *Regulation of Leukocyte Function*, R. Snyderman, ed., Plenum Publishing Corp., pp. 109–153.

Because of its proinflammatory activity, C5a has been implicated as a pathogenic factor in the expression of certain inflammatory disorders, such as rheumatoid arthritis, adult respiratory distress syndrome, gingivitis, and the tissue damage associated with atherosclerosis and myocardial infarction. Consequently, considerable research efforts have been expended in developing specific C5a antagonists for use as anti-inflammatory agents in the treatment of these diseases.

One approach to the development of a potent C5a antagonist has focused on the synthetic manipulation of peptides possessing sequence homology to the C-terminal "effector" region of C5a. These peptides have been shown to be effective agonists compared to the parent polypeptide, but at markedly reduced potencies (see, e.g., Ember et al. (1994), Amer. J. Pathol., 144: 393–403; Ember et al. (1992), J. Immunol., 148: 3165–3173; Morgan et al. (1992), J. Immunol., 148: 3937–3942). Therefore, a first step toward the development of an antagonist would be to increase the potency of these agonist peptides to a level approaching that of natural C5a, the rationale being that the increase in potency reflects a heightened affinity for the C5a receptor. Such potent peptide agonists could be used as templates from which an analog or mimetic is developed-that would retain the high affinity binding characteristics, so as to compete with natural C5a for the receptor, but not transduce a biological signal when bound to the receptor.

On the other hand, C-terminal agonists of C5a have been shown to induce the synthesis and release of several immune-modulatory cytokines from human monocytes (see Goodman et al. (1982), J. Immunol., 129: 70–75; Okusawa et al. (1987), J. Immunol., 139: 2635–2639; Scholz et al. (1990), Clin. Immunol. Immunopathol., 57: 297–307; Ember et al. (1994), Amer. J. Pathol., 144: 393–403). Because of its multiple roles in the cellular and humoral immune response, considerable interest also exists in developing specific C5a agonists as immune adjuvants for treatment of immunocompromised patients.

Ideally, C5a agonists or antagonists would not only be potent, but would be selective for a specific desired biological response associated with naturally-occurring C5a. For example, an analog that could stimulate the immune-modulatory effect in monocytes at the expense of other C5a-mediated inflammatory responses would have considerable therapeutic utility as an immune adjuvant for stimulating cellular and humoral immune responses, but exhibiting no inflammatory side effects. As another example, C5a has been shown to have a direct effect on rat pulmonary artery endothelial cells, implying the presence of functional C5a receptors on these and other endothelial tissues (Friedl et al. (1989), FASEB J., 3: 2512–2518; Ward (1991), Am. J. Med., 91 (Suppl. 3C): 89S–94S). Accordingly, another therapeutic utility for a selective agonist would be an analog that could select for these endothelial C5a receptors to induce a direct, transient increase in vascular permeability without involving circulating neutrophils. A direct increase in vascular permeability would be useful to augment the delivery of large macromolecules (e.g., monoclonal antibodies) from the blood to surrounding diseased tissue, or across the blood-brain barrier, but not engage neutrophils or their accompanying side effects (adhesion, enzyme release, superoxide release, chemotaxis).

As mentioned, several C-terminal C5a peptide analogs have been produced and studied for the purpose of developing C5a agonists and antagonists. For example, Ember et al. (1992, supra), characterized the biological activities of 22 synthetic C-terminal C5a analogs. The analogs were reported to be full agonists of natural C5a, having in vitro activities characteristic of naturally occurring C5a, including the ability to stimulate ileal contraction (i.e., spasmogenesis) platelet aggregatory activation and neutrophil polarization and chemotaxis. However, the potencies of even the most effective of these analogs was on the order of only .0.01–0.25% that of the natural factor. This level of potency could be obtained with analogs as short as decapeptides, as compared with longer C-terminal peptides that had previously been studied as potential agonists. Morgan et al. (1992, supra) reported that certain of the peptide analogs disclosed by Ember et al. stimulated synthesis of interleukin-6 in human peripheral blood mononuclear cells. Again, however, potency of these peptide analogs was on the order of 0.01–0.1% of either natural or recombinant C5a. Drapeau et al. reported on the pharmacology, metabolism and in vivo cardiovascular and hematologic effects of synthetic C-terminal C5a peptide analogs based on either human or porcine amino acid sequences. These analogs were also found to be agonists of natural C5a, but were disclosed as being at least 1,000-fold less potent than recombinant C5a as measured by competition for C5a binding sites.

Each of the aforementioned reports describes differences among the various peptide analogs with respect to their effectiveness for eliciting specific biological responses associated with C5a. However, the basis for that differential elicitation of biological response was not described with respect to specific structure-function relationships.

C-terminal C5a peptide analogs have also been studied with respect to the ability of such analogs to bind to C5a receptors. Kawai et al. (1992), J. Med. Chem., 35: 220–223, reported on relationships between the hydrophobicity and chirality of residues 70–73 of C-terminal octapeptide analogs and the ability of such analogs to bind to C5a receptors. However, biological responses elicited by these octapeptide analogs was not reported. In other studies, it has been determined that substitution of phenylalanine or tryptophan in positions between 65 and 69 of the human C5a C-terminus could enhance or decrease potency, depending on whether the substitution was made at position 67 or at position 66. In other studies, these observations were corroborated with reports that substitution of phenylalanine for histidine at position 67 substantially increased the potency of a number of C-terminal peptide analogs of human C5a. See Mollison et al. (1991), Agents and Actions, Suppl. 35: 17–21; Or et al. (1992), 35: 402–406; Köhl et al. (1993), Eur. J. Immunol., 23: 646–652. These reports did not address any differences among the various peptide analogs with respect to their effectiveness for eliciting specific biological responses associated with C5a, although it was noted that different tissue or cell types and different species responded differently to the analogs.

Thus, in spite of the numerous C-terminal peptide analogs that have been synthesized and studied to date, no effective peptide-based C5a agonist or antagonist, either general or selective, has been reported. This is in part due to the hitherto unclear relationship between the conformational features of the C-terminal peptides and the biological properties they impart, which has impeded the progress of a rational design strategy for the development of a high-affinity and selective C5a analog.

The general spatial arrangement of the N-terminal region of human C5a (residues 1–63) has been determined on the basis of $^1$H-NMR data, but no definable spatial structure could be assigned to the C-terminal "effector" region (residues 64–74), which appears more flexible than the rest of the C5a polypeptide (Zuiderweg et al. (1989), Biochem., 28: 172–185). Flexibility in the C-terminal region appears to play a role in potency and general expression of biological activity because marked changes in potency have been observed when the flexibility in this region was restricted (Ember et al., 1992, supra, reporting that modifications made in the C-terminal portion of the C5a peptide analogs to reduce flexibility of the backbone affected their activity).

To date, however, the structure-function relationship of the C-terminal portion of C5a and its biological activities has not been successfully exploited to develop more potent agonists, nor has it been utilized to produce agonists with selective activities, i.e., the ability to elicit specific biological responses (e.g., spasmogenic response) in favor of others (e.g., neutrophil-mediated responses). Thus, a need exists to develop more potent C5a agonists and, further,.to produce high-affinity C5a analogs having biological response-selective agonistic activity. Such compounds will find broad utility in treating immunocompromised patients, preferably without inflammatory side effects, and as high affinity templates for the development of antagonists to modulate pathological diseases associated with the proinflammatory activities of C5a.

SUMMARY OF THE INVENTION

In accordance with the present invention, compounds are provided which comprise oligopeptide analogs of the carboxy-terminal "effector" region of C5a. These C5a analogs are not only significantly more potent than other analogs heretofore reported, but also are response-selective to elicit different classes of biological responses associated with C5a.

According to one aspect of the invention, a compound is provided which comprises an oligopeptide analog of a C5a carboxyl terminus; the analog includes a C-terminal segment having a constrained backbone conformation comprising a β-turn. Such a compound is capable of binding to a C5a receptor and expressing at least one biological activity of C5a (i.e., elicitation of a biological response associated with natural C5a). Whereas natural C5a has considerable flexibility in the C-terminal region, the analogs of the invention are constrained at their C-termini into a β-turn backbone conformation. In accordance with the present invention, it has been discovered that a stabilized β-turn conformation at the C-terminus confers a marked increase in potency of the oligopeptide analogs of the invention. Moreover, the particular β-turn motif of the constrained C-terminal backbone conformation confers the response-selectivity of the C5a analogs of the invention.

Preferred compounds of the present invention comprise decapeptide analogs of the C5a carboxy-terminus which, in addition to the C-terminal constrained β-turn, further comprise an N-terminal segment having a helical backbone conformation and a central segment, disposed between the N-terminal segment and the C-terminal segment, which has an elongated backbone conformation.

According to another aspect of the present invention, compounds are provided in which the constrained C-terminal segment of the above-described oligopeptide analog is a β-turn selected from the group consisting of type II and type V β-turns. These compounds selectively elicit a group of biological responses referred to herein as "Class 1" proinflammatory responses, characterized by spasmogenesis, platelet aggregation and neutrophil non-mediated increases of cell-membrane permeability (specifically, vascular permeability).

Similarly, according to another aspect of the present invention, compounds are provided in which the constrained C-terminus of the above-described oligopeptide analogs comprise a β-turn selected from the group consisting of type III' β-turns and an undefined β-turn characterized by a tetrapeptide (or analog thereof) occupying Ramachandran quadrants B, L, H, B/R for residues 1–4, respectively, of the tetrapeptide. These compounds selectively elicit a biological response referred to herein as a "class 2" proinflammatory response, characterized by neutrophil polarization, neutrophil enzyme release and neutrophil-mediated increases in cell membrane permeability (especially vascular permeability).

According to another aspect of the present invention, compounds are provided having the formula:

A1-Ser-Phe-Lys-A2-A3-A4-A5-A6-A7, wherein

- A1 is Tyr, Trp or N-acetylated derivatives thereof;
- A2 is Asp, Gly, Pro or N-methyl derivatives of Asp or Gly;
- A3 is Ala, Cys, Leu, Met or N-methyl derivatives of Ala, Cys, Leu or Met;
- A4 is Gln, Leu, Pro or N-methyl derivatives of Gln or Leu;
- A5 is Leu, N-methyl Leu or Pro;
- A6 is D-Ala, Gly, D-Pro, Aib, or N-methyl derivatives of D-Ala or Gly; and
- A7 is Arg or N-methyl Arg.

Preferred compounds of the present invention that selectively elicit "class 1" proinflammatory responses such as spasmogenesis, platelet aggregation and neutrophil non-mediated cell membrane permeability increases, are also provided. These compounds have the general formula:

A1-Ser-Phe-Lys-A2-A3-A4-A5-A6-A7, wherein:

- A1 is Tyr, Trp or N-acetyl derivatives of Tyr or Trp;
- A2 is Asp, Gly, Pro or N-methyl derivatives of Asp or Gly;
- A3 is Ala, Cys, Met or N-methyl derivatives of Ala, Cys or Met;
- A4 is Pro;
- A5 is Leu or N-methyl Leu;
- A6 is D-Ala, Gly, D-Pro, or N-methyl derivatives of D-Ala or Gly; and
- A7 is Arg or N-methyl Arg.

In another preferred embodiment, compounds are provided which selectively elicit the "class 2" proinflammatory responses, such as neutrophil polarization, neutrophil enzyme release and neutrophil-mediated increases in cell membrane permeability. These compounds have the formula:

A1-Ser-Phe-Lys-A2-A3-A4-A5-A6-A7, wherein:

- A1 is Tyr, Trp or N-acetyl Tyr or Trp;
- A2 is Asp, Gly, Pro or N-methyl derivatives of Asp or Gly;
- A3 is Leu, Met or N-methyl derivatives of Leu or Met;
- A4 is Gln, Leu, Pro or N-methyl derivatives of Gln or Leu;
- A5 is Pro, Leu, a-methyl Leu or N-methyl Leu;
- A6 is D-Ala, Gly, D-Pro or N-methyl derivatives of D-Ala or Gly; and
- A7 is Arg or N-methyl Arg.

Compounds having the conformations and comprising the formulae set forth hereinabove are high-potency C5a analogs that can selectively elicit different classes of biological responses associated with natural C5a. These high-potency analogs may be used as agonists to selectively elicit desired. biological responses associated with natural C5a, and will find broad utility in treating immunocompromised patients, preferably without inflammatory side effects. These compounds will also find wide utility as high-affinity templates for the development of C5a antagonists to modulate pathological conditions associated with the various proinflammatory activities of C5a.

BRIEF DESCRIPTION OF THE DRAWINGS

FIG. 1. Dose-response curves for human recombinant C5a and agonist peptides in human-fetal artery. Tissue strips were exposed to single concentrations of C5a or peptides and, following contraction, exposed to a supramaximal concentration of histamine (10 μM). Closed circles=C5a; (x—x)=C-terminal 19-mer of natural human C5a. (o—o)= Peptide 2 (YSFKDMQLGR; Sequence I.D. No. 2), demonstrating the effect of substitution of Phe-67 for His-67. Closed squares=peptide 10 (YSFKDMPLaR; Sequence I.D. No. 10), showing the increased potency induced by the dual substitutions of Pro-71 and D-Ala-73. Points represent the mean response and the vertical bars the SEM. n=6–8 experiments in each group.

FIG. 2. Ramachandran plot showing the sterically allowed conformational space occupied by the amino acid residues in the decapeptide $C5a_{65-74}$. (The terminal residues 65 and 74 are omitted). Sterically allowed space for L- and D-residues are contained within the solid and hashed lines respectively. The narrow, vertical regions depict the allowed space for L-Pro (left hand quadrants outlined with solid lines) and D-Pro. (right hand quadrants outlined with dashed lines). The boxed region in quadrant B is the allowable conformational space for the pre-proline residues. B, R, L and H refer to the (ϕ,Ψ) regions that correspond to β-structure, right handed helices, left handed helices, and high energy structure respectively.

FIG. 3. Stereoview of the decapeptide agonist $C5a_{65-74}$Y65,F67 (YSFKDMQLGR; Sequence I.D. No. 2) showing the helix-like conformation for Tyr-65 to Asp-69, elongated conformation for Met-70 to Gln-71, and β-turn type II for (Gln-71)Leu-72 to Arg-74.

FIG. 4. Correlation between effective peptide concentrations in fetal artery and platelet aggregation (numbers on graph are Sequence I.D Numbers). Abscissa: mean pD2 values for peptides in. fetal artery. Ordinate: Threshold concentration of peptides causing platelet aggregation. Regression coefficient (r)=0.84, n=23.

FIG. 5. Correlation between pD2 values for peptides and C5a in fetal artery, ileum and lung parenchyma. Abcissa: pD2 values in fetal artery. Ordinate: pD2 values in ileum (o) and parenchyma (+). Data derived from Table .2. Fetal artery versus ileum., r=0.95 (n=7); fetal artery versus lung parenchyma, r=0.98 (n=5).

FIG. 6. Correlation between effective concentrations for peptides and C5a in guinea-pig platelets, ileum and lung parenchyma. Abcissa: Threshold concentration causing platelet aggregation. Ordinate: pD2 values in ileum (o) and parenchyma (+). Data derived from Table 2. Platelet aggregation versus ileum, r=0.99 (n=7); platelet aggregation versus lung parenchyma, r=0.99 (n=5).

FIG. 7. Correlation between effective concentrations for peptides and C5a in human PMN polarization and enzyme release from human PMNs. Abcissa: pD2 values for PMN enzyme release (EC50, log [(peptide (μM)]. Ordinate: pD2 values for PMN polarization (EC50, log [peptide (μM)]. Data derived from Table 4. PMN polarization versus PMN enzyme release, r=0.99 (n=3).

FIG. 8. Ramachandran plot showing the sterically allowed conformational space occupied by the residues in $C5_{65-74}$ (terminal residues 65 and 74 are omitted). Sterically allowed space for L- and D-residues are contained within the solid and hashed lines respectively. The narrow, vertical regions depict the allowed space for L-Pro (left hand quadrants outlined with solid lines) and D-Pro (right hand quadrants outlined with dashed lines). The boxed region in quadrant B is the allowable conformational space for the pre-proline residues. B, R, L and H refer to the (φ,Ψ) regions that correspond to β-structure, righthanded helices, lefthanded helices, and high energy structure, respectively. This Ramachandran plot is similar to that shown in FIG. 3 except that a conformational change of Leu-72 from the B quadrant to the L quadrant appears to favor expression of PMN activities.

Figure 9B:
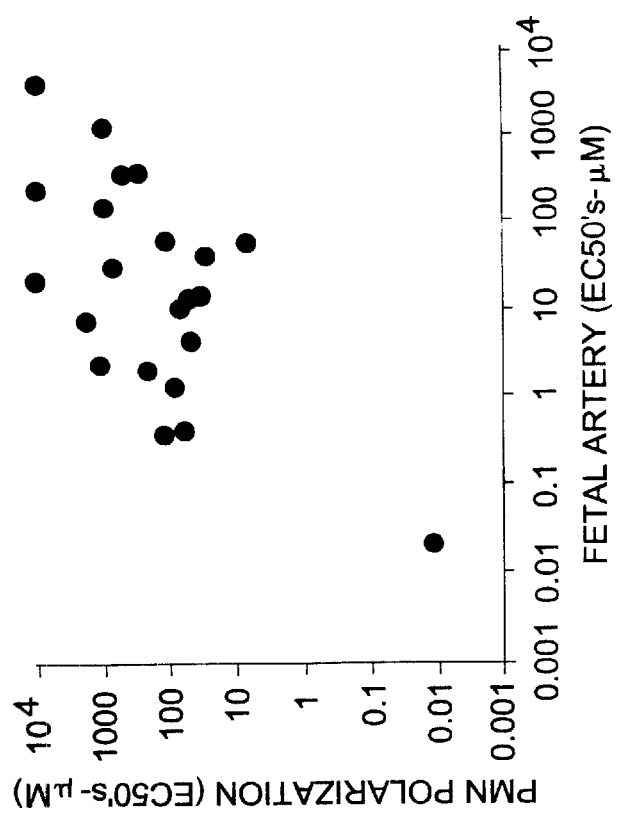
Figure 9A:
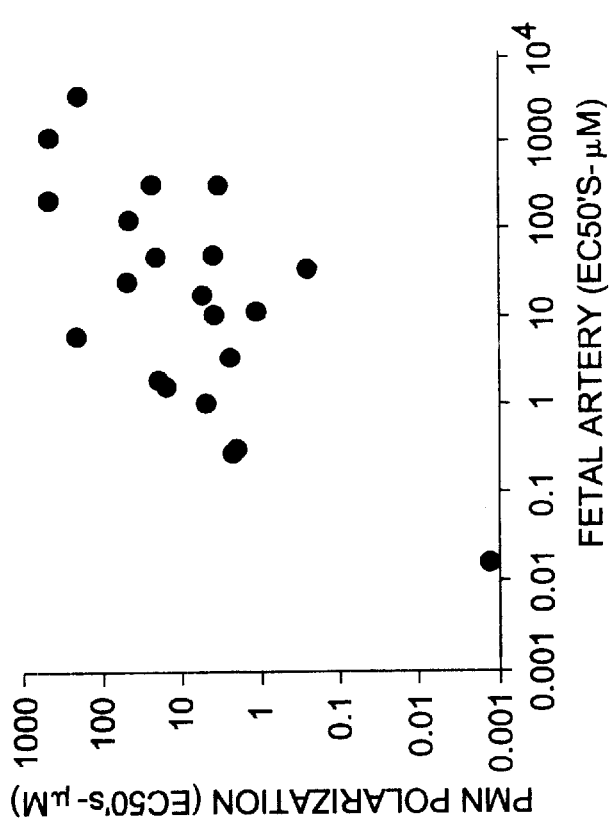

FIG. 9. Correlations between Class 1 and Class 2 proinflammatory biological responses. FIG. 9A: Correlation between PMN polarization and contraction of human fetal artery. FIG. 9B: Correlation between enzyme release from PMNs and contraction of human fetal artery. Abcissa: pD2 values in fetal artery (EC50, log [peptide ($\mu$M)]). Ordinate: (FIG. 9A): pD2 values for PMN polarization (EC50, log [peptide ($\mu$M)].); Abcissa (FIG. 9B): pD2 values for PMN enzyme release (EC50, log [peptide ($\mu$M)]).

Figure 10:
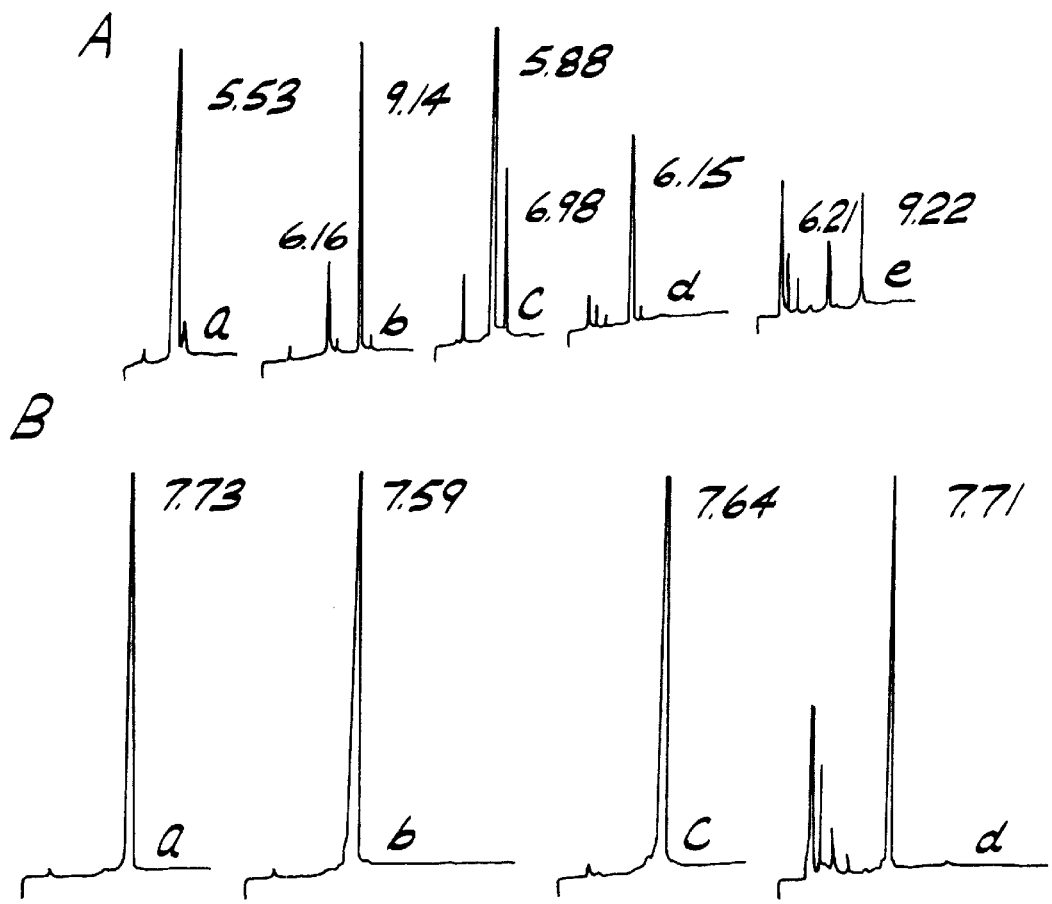

FIG. 10. HPLC profiles of decapeptide analogs. FIG. 10A: HPLC of YSFKDMQLGR (peptide/Sequence I.D. No. 2); a=purified peptide; b=des-Arg peptide (YSFKDMQLG; Sequence I.D. No. 24); c=des-Arg peptide in saline, no incubation; d=des-Arg peptide in saline with incubation for 1 h at 37° C.; e=des-Arg peptide in normal human serum with incubation for 1 h at 37° C. FIG. 10B: HPLC of YSFKDMPLaR (Sequence I.D. No. 10); a=purified peptide; b=peptide in saline, no incubation; c=peptide in saline with incubation for 1 h at 37° C.; d=peptide in normal human serum with incubation for 1 h at 37° C. Solvent system 1: 70 mM triethylamine/phosphoric acid buffer, pH-2.3. Solvent system 2: 60% acetonitrile in the Solvent 1 buffer. Linear gradient of 30–50% solvent 2 at.1%/min, slope=1 ml/min, absorbance monitored at 214 nm.

DETAILED DESCRIPTION OF THE INVENTION

In accordance with the present invention, it has now been determined that C-terminal peptide analogs of C5a, whose naturally flexible structure has been modified to constrain the peptides to specific conformations, are not only manyfold more potent than previously-described peptide analogs, but also exhibit the ability to selectively stimulate different classes of biological responses associated with C5a.

As mentioned above, no definable spatial structure has been assigned previously to the C-terminal "effector" region (residues 64–74) of C5a, due to the flexibility in backbone conformation of this region. However, based on a detailed analysis of the sequential d-connectivities from the NMR data on human C5a reported by Zuiderweg et al., 1989, supra, we were able to distinguish general structural features of the C-terminal decapeptide region, $C5a_{65-74}$, the amino acid sequence of which comprises Ile-Ser-His-Lys-Asp-Met-Gln-Leu-Gly-Arg (Sequence I.D. No. 1). To accomplish this, we used a probablistic approach to analysis of NMR data, involving the FISINOE-2 program of NMR data analysis, which is an improved of the FISINOE program that was developed by Sherman et al. (J. Mag. Reson., 96: 457–472, 1992). Both FISINOE and FISINOE-2 make use of observed NOE parameters and coupling constants in conjunction with empirical φ, Ψ probability distribution functions. Both PROFOLD and FISINOE are described in greater detail in Example 1 herein.

From this analysis, we distinguished three general structural features of the C-terminal decapeptide region, $C5a_{65-74}$. The region comprised of residues Ile-65 to Lys-68 or Asp-69 was consistent with a twisted, helix-like structure and the region made up of Asp-69 or Met-70 to Gln-71 possessed an elongated backbone conformation. The C-terminal region of $C5a_{65-74}$, comprised of residues Leu-72 to Arg-74, was considerably more flexible than the rest of the peptide and appeared to be made up of overlapping structural contributions of both twisted and elongated conformations. We have determined that flexibility in the C-terminal regions (residues 71–74) is important in the selective stimulation of biological responses because dramatic changes (both positive and negative) in activity and potency are observed when the flexibility in this region is restricted (Sanderson et al., Abstract presented at the 13th American Peptide Symposium, Jun. 20–25, 1993; Taylor et al. (1993), Clin. Exp. Pharm. Physiol. Supp., 1: A72). However, the specific conformations leading to increased potency and selective elicitation of particular biological responses were heretofore unexplored.

In accordance with the present invention, we have performed a structure-function analysis of a panel of decapeptide analogs of human $C5a_{65-75}$ synthesized with residue substitutions that restrict flexibility in the C-terminal region of the peptide (residues 69–74). These conformationally constrained analogs were generated in order to determine the most likely conformation(s) that are responsible for the increased potency and expression of different various classes of biological responses. From this analysis, we learned that a β turn in the C-terminal region (residues 71–74) conferred significantly increased potencies to the peptide analogs. More notably, however, the type of β turn in that region was found to correspond with a selective elicitation of a specific biological response. For example, for the expression of spasmogenic activity in human fetal artery, guinea pig ileum and guinea pig lung parenchyma and for aggregatory activity of guinea pig platelets, we identified a characteristic C-terminal, turn-like motif that was consistent with a β-turn of type II or V for the region comprising residues 71–74. Analogs that expressed a structural propensity to this C-terminal motif appeared particularly potent relative to C5a in this class of biological respdnses. For the expression of neutrophil polarization, neutrophil degranulation and release of enzymes from neutrophils, we identified a characteristic C-terminal turn-like motif that was consistent with a β-turn of type III' for the region comprising residues 71–74. Analogs expressing a structural propensity to this C-terminal motif appeared particularly potent as compared with C5a in this class of biological responses. The experimental basis for these findings is set forth in greater detail in Examples 1–3.

Thus, we have characterized a common, preferred backbone conformation in a series of C-terminal decapeptide analogs of human C5a that confers increased potency and correlates with the expression of specific classes of biological responses. The ability of C5a or a peptide analog to elicit such responses is sometimes referred to herein as "biological activity" of C5a or analogs thereof. We have also identified analogs from a panel of 23 peptide analogs that selectively elicit specific classes of biological responses due to their structural propensity to a particular motif in the β-turn portion of the C-terminal conformation. Peptide analogs that exhibit such response-selective agonistic activity are sometimes referred to herein as "selective agonists" or "response-selective agonists." These selective agonists are categorized broadly by their respective abilities to stimulate (1) the class of proinflammatory biological responses associated with spasmogenesis and a direct effect on vascular permeability, (2) the class of proinflammatory responses associated with human neutrophil activation (such activation also plays a role in vascular permeability) or (3) the class of biological responses associated with regulation of the human immune system. The class of proinflammatory biological response typified by the spasmogenic response is referred to herein as a "Class 1" proinflammatory response. This response is measured and characterized by various in vivo and in vitro assays, which include spasmogenic responses (i.e., smooth muscle contraction) of human fetal artery, guinea-pig ileum or lung parenchyma, and guinea-pig platelet aggregation. The human neutrophil-mediated biological responses are sometimes referred to herein as "Class 2" proinflammatory responses, and are measured and characterized by various in vivo and in vitro assays, including neutrophil polarization, neutrophil chemotaxis, neutrophil degranulation and release of enzymes (e.g., β-glucuronidase). Additionally, C5a activities directed to modulation of the immune system (i.e., stimulation of monocytes to release immunostimulatory cytokines, such as IL-1, IL-6, IL-8 and tumor necrosis factor (TNF-α) are sometimes referred to herein as "immunomodulatory (or immunoregulatory) activities (or responses"). The classes of biological responses and assay methods listed above are intended to illustrate, and not to limit, the invention. C5a may act on (or interact with) membrane non-associated moieties as well, such as enzymes and or other regulatory molecules involved in the immune response (e.g., C5 convertase). Such other types of biological responses elicited by. C5a may also be selected for by designing appropriate peptide analogs in accordance with the present invention.

Sections I–III below set forth details and preferred embodiments for practicing the present invention, including: (1) methods for selecting appropriate C-terminal-residues to achieve the desired constrained conformation for a response-selective agonist; (2) methods for producing the peptide analogs, as well as the response-selective peptide analogs produced by those methods; (3) methods for testing the peptide analogs for their ability to selectively stimulate a specific biological response; and (4) methods of using the selective peptide agonists as immune adjuvants, as adjuncts for increasing vascular permeability or as high affinity templates for the development of selective C5a antagonists.

In the description that follows, unless otherwise specified, standard methods are used for peptide synthesis and characterization. To the extent that other specific materials are mentioned, it is merely for purposes of illustration and is not intended to limit the invention.

I. Designing and Producing Potent, Response-Selective C5a Peptide Agonists

Once a particular desired conformation of a short peptide has been ascertained, methods for designing a peptide or peptidomimetic to fit that conformation are well known in the art. See, e.g., G. R. Marshall (1993), Tetrahedron, 49: 3547–3558. The Ramachandran plot is particularly useful for the designing of short peptides in which at least a portion of the peptide comprises a β-turn. The use of the Ramachandran plot for peptide design has been reviewed generally by Hruby & Nikiforovich (.1991), in *Molecular Conformation and Biological Interactions*, P. Balaram & S. Ramasehan, eds., Indian Acad. of Sci., Bangalore, pp. 429–445. As discussed in pages 434–435 of Hruby & Nikiforovich, any one of the several types of β-turns may be examined within the constraints of the Ramachandran plot, for the purpose of designing peptides comprising such β-turns.

The design of agonistic peptide analogs may be further refined by considering the contribution of various side chains of amino acid residues (i.e., for the effect of functional groups or for steric considerations). Methods for combining Ramachandran plot constraints with predictions of side chain effects are well known in the art, and have been practiced by protein biochemists for many years (see, e.g., Hruby & Nikoforovich at pages 436–442; see also G. R. Marshall, 1993, supra.) In accordance with the present invention, a high-affinity analog of the carboxy-terminal effector region of C5a comprises a basic backbone conformation as follows: (1) an N-terminal portion (preferably including at least 3 amino acid residues or isosteric mimetics), which comprises a helical conformation; (2) a central portion (preferably comprising at least two residues or mimetics) having an elongated conformation; and (3) a C-terminal portion (preferably of at least 3 amino acid residues or mimetics thereof) that comprises a β-turn. In correspondence with the C-terminus of human C5a, for example, the aforementioned N-terminal portion corresponds to residues 65–68 or 69; the central portion corresponds to residues 69 or 70–71; the C-terminal portion corresponds to residues 71–74. Of these three features, the analog should at minimum possess a conformationally stabilized β turn in the C-terminal portion, since the presence of a β turn at that location increases the overall potency of such analogs well beyond reported for any other C-terminal C5a analogs, and also provides the basis for imparting response selectivity (see Examples 1–3).

Within the constraints of the backbone conformation described above, as well as considerations of the effects of side chain functionalities, it will be appreciated by those of skill in the art that a peptide mimic may serve equally well as a peptide for the purpose of providing the specific backbone conformation required for binding to C5a receptors and eliciting appropriate biological responses. Accordingly, it is contemplated as being within the scope of the present invention to produce C5a analogs having the above-described conformational features through the use of naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic," or sometimes as an "isosteric peptidomimetic" to designate substitutions or derivations of peptide-based C5a analogs that possess the same backbone conformational features and/or other functionalities.

The use of isosteric peptidomimetics for the development of high-affinity and/or selective peptide analogs is well known in the art. (see, e.g., Hruby & Nikiforovich, 1991, supra at page 437–438). Of particular relevance to the present invention, mimics of peptide backbone structures, such as α-helices, β-turns and β sheets have been developed. For example, Kemp et al. (Tetrahedron Lett., 29: 5057–5060, 1988) disclose derivatives of dilactams of L-α, γ-diaminobutyric acid and D-glutamic acid as a constrained β-turn template, particularly for the selective stabilization of type II β-turns. Kahn et al. (J. Amer. Chem. Soc., 110: 1638–1639, 1988) disclose a non-peptide mimetic of β-turns produced by oxidative intramolecular cycloaddition of an azodicarbonyl system. As another example, Olson et al. (J. Amer. Chem. Soc., 112: 323–333, 1990) disclose a model tetrapeptide mimetic of a type II' β-turn produced from a 9-membered ring lactam system. Numerous other peptide mimetic structures useful for the practice of the present invention are available and will be apparent to those of skill in the art.

See, e.g., *Peptides: Chemistry, Structure and Biology* (1990), J. E. Rivier & G. R. Marshall, eds., ESCOM Publishers, Leiden, Netherlands (specifically, Kahn et al., pp 498–500; Kemp et al., pp 861–864; and Nicolaou et al., pp 881–884). Assuming-rotational constraints similar to those of amino acid residues within a peptide, analogs comprising non-amino acid moieties may be analyzed, and their conformational motifs verified, by means of the Ramachandran plot (see Hruby & Nikiforovich, supra).

It has also been discovered in accordance with the present invention that, suprisingly, the specific structure of the C-terminal portion (i.e., the particular type of β-turn) plays an important role in the selectivity of the peptide analog for eliciting a particular biological response. Accordingly,. exemplary peptides of the invention may be designed that differ with respect to the type of β-turn. comprising the C-terminal portion. For example, referring to the C-terminal β-turn motif of human C5a analogs, as described in examples 1–3, exemplary analogs that elicit a class 1 biological response are designed to possess a C-terminal β-turn of type II or V. In terms of Ramachandran plot analysis (see FIG. 3) residues corresponding to residues 71–74 of human C5a, the favorable Ramachandran space occupied by these residues for a Class 1 response is B(71), B(72), L(73), B/R(74) (type II β-turn) or B(71), B(72), H(73), B/R(74) (type V β-turn) (numbers refer to the residue number of the human C5a protein sequence). Any amino acid or isosteric mimetic substitution in this 4-residue peptide that results in the backbone occupying these favorable Ramachandran spaces is contemplated for use in the present invention, to produce potent C5a analogs that selectively elicit the Class 1 biological responses.

Similarly, exemplary human C5a analogs that selectively elicit the Class 2 biological responses comprise a C-terminal β-turn wherein the favorable Ramachandran space occupied by this portion of the peptide is B(71), L(72), L(73), B/R(74) (type III' β-turn) or B(71), L(72), H(73), B/R(74) (undefined β-turn). Again, any naturally-occurring peptide or isosteric mimetic is contemplated for use in designing and producing potent, Class 2 response-selective C5a analogs having conformations that fall into the aforementioned favorable Ramachandran spaces.

Within the parameters discussed above, several exemplary decapeptide analogs of the human C5a C-terminal effector region have been synthesized which have been found to be potent, selective agonists for elicitation of proinflammatory responses falling into either "Class 1" responses (e.g., spasmogenic, platelet aggregatory) or "Class 2" responses (e.g., neutrophil polarization, enzyme release), respectively. As described in detail in Examples 1–3 herein, these peptides can be described generally by the formula:

A1-Ser-Phe-Lys-A2-A3-A4-A5-A6-A7, wherein:
A1 is Tyr, Trp or an N-acetyl derivative thereof;
A2 is Asp, Gly or Pro;
A3 is Ala, Cys, Leu or Met;
A4 is Gln, Leu or Pro;
A5 is Leu or Pro;
A6 is D-Ala, Gly, D-Pro or aminoisobutyric acid (Aib); and
A7 is Arg or N-methyl Arg.

With respect to A1, it is known that, in addition to Tyr, the use of Trp or an N-acetylated N-terminal residue can increase the potency of C5a oligopeptide analogs to a modest extent (see Kawai et al., 1992, supra; Kohl et al., 1993, supra). With respect to A6 and A7, the use of Aib and N-methylated amino acid derivatives is discussed in greater detail below.

Within the general formula set forth above, exemplary peptides that are selectively potent for eliciting the Class 1 proinflammatory response comprise the following substituents:

A3 is Ala, Cys or Met;
A4 is Pro; and
A5 is Leu.

A complete discussion of these specific peptide analogs of human C5a is set forth in Example 2.

The following decapeptides have been found particularly useful as potent agonists for eliciting the Class 1 proinflammatory response:

Tyr-Ser-Phe-Lys-Pro-Met-Pro-Leu-(D-Ala)-Arg (Sequence I.D. No. 24);
Tyr-Ser-Phe-Lys-Asp-Ala-Pro-Leu-(D-Ala)-Arg (Sequence I.D. No. 19);
Tyr-Ser-Phe-Lys-Asp-Met-Pro-Leu-(D-Ala)-Arg (Sequence I.D. No. 10);
Tyr-Ser-Phe-Lys-Gly-Met-Pro-Leu-Gly-Arg (Sequence I.D. No. 23);
Tyr-Ser-Phe-Lys-Asp-Met-Pro-Leu-Gly-Arg (Sequence I.D. No. 5);
Tyr-Ser-Phe-Lys-Asp-Ala-Pro-Leu-Gly-Arg (Sequence I.D. No. 15);
Tyr-Ser-Phe-Lys-Asp-Cys-Pro-Leu-Gly-Arg (Sequence I.D. No. 16).
Tyr-Ser-Phe-Lys-Asp-Met-Pro-Leu-(D-Pro)-Arg (Sequence I.D. No. 14).

Remarkably, Sequence I.D. No. 24 above has been found to be within 20–30% the potency of naturally-occurring C5a for the elicitation of a spasmogenic response (Class I) and Sequence I.D. No. 19 is within 4–5% of natural C5a potency in this respect. These, and the other sequences listed above which all exhibit potency within at least about 1% of natural C5a, are believed to be the most potent C5a agonists ever produced.

As described in Example 3 herein, exemplary C5a decapeptide analogs which are capable of selectively eliciting a Class 2 proinflammatory response include substituents wherein:

A3 is Leu or Met;
A5 is Leu, α-methyl Leu-or Pro; and
A6 is D-Ala, Gly or D-Pro.

Specific exemplary decapeptides include:
Tyr-Ser-Phe-Lys-Gly-Leu-Leu-Leu-Gly-Arg (Sequence I.D. No. 21);
Tyr-Ser-Phe-Lys-Asp-Met-Gln-Leu-(D-Ala)-Arg (Sequence I.D. No. 8);
Tyr-Ser-Phe-Lys-Gly-Met-Pro-Leu-Gly-Arg (Sequence I.D. No. 23);
Tyr-Ser-Phe-Lys-Asp-Met-Pro-Leu-(D-Pro)-Arg (Sequence I.D. No. 14);
Tyr-Ser-Phe-Lys-Asp-Met-Gln-Leu-Gly-Arg (Sequence I.D. No. 2);
Tyr-Ser-Phe-Lys-Asp-Met-Gln-Pro-Gly-Arg (Sequence I.D. No. 4).

The most potent of these peptides are within about 0.1–0.4% of full C5a biological activity in PMN polarization assays and within about 0.04–0.18% of natural C5a in PMN enzyme release assays.

The above-described analogs comprise amino acid residues found in naturally-occurring proteins. However, these peptides are intended to illustrate and not to limit the invention. As mentioned, non-protein residues or amino acid homologs and derivatives are also useful in constructing peptidomimetic analogs of the invention. As described in Example 5, for example, the substitution of α-aminoisobutyric acid (Aib) at the position corresponding to residue 73 of human C5a, to form the decapeptide:

Tyr-Ser-Phe-Lys-Asp-Met-Gln-Leu-Aib-Arg (Sequence I.D. No. 25) will produce an analog having a type II or type V β-turn in the C-terminal portion. This analog can be used directly, or it may also be used for further elucidation of the precise nature of conformational and other functional features responsible for the response-selectivity of the analogs.

As another example, a peptide may be produced having the sequence:

Tyr-Ser-Phe-Lys-Asp-Met-Gln-Leu-(D-Ala) (NMe)Arg (Sequence I.D. No. 26), where NMe signifies that the amide nitrogen between D-Ala and Arg is methylated. The presence of the methylated amide nitrogen between positions 73 and 74 of human C5a is predicted to lock the backbone conformation of the C-terminal portion of the peptide analog into the type II or type V conformation β-turn, and the effect of such a peptide in eliciting Class 1 proinflammatory responses will elucidate whether the type II or type V turn is more conducive to the Class 1 response-selective activity of the analog.

The leucine derivative, α-methylleucine (L (α-Me)) may be used to advantage in the design of peptides for specifically eliciting neutrophil-mediated biological responses (i.e., Class 2 responses). Thus, a peptide such as:

Tyr-Ser-Phe-Lys-Asp-Met-Gln-L(α-Me)-(D-Ala)-Arg (Sequence I.D. No. 27) may be synthesized. The presence of the methyl group on the alpha carbon of the leucine at position 72 (corresponding to human C5a) forces the backbone conformation at this site into the L quadrant of the Ramachandran plot, thereby forming a 4-residue C-terminus consistent with a β turn of type III'. Such a peptide is designed to specifically increase Class 2 biological responses, such as PMN polarization and enzyme release. The synthesis of such a peptide is described in Example 5 herein.

One N-methylated peptide was described hereinabove with respect to producing a peptide to specifically elicit Class 1 biological responses. Other N-methylpeptides may be generated for biasing a specific backbone conformation (i.e., β-turn) in a manner similar to the presence of Pro, yet will allow assessment of the importance of various sidechains of the peptide analogs in response-selective agonistic behavior. For example, the peptide:

Tyr-Ser-Phe-Lys-Asp-Met-Gln-Leu-(D-Ala)(NMe)Arg (Sequence I.D. No. 28) will bias a particular type of β-turn and allow the side chain of Arg (position 74 of human C5a) to interact with receptors and/or other moieites. As another example, the peptide Tyr-Ser-Phe-Lys-Asp-Met-Gln-Leu(NMe)(D-Ala)-Arg (Sequence I.D. No. 29) will bias a particular type of β-turn and allow the side chain of D-Ala at position 73 of the human C5a to interact with receptors and/or other moieties; the peptide Tyr-Ser-Phe-Lys-Asp-Met-Gln(NMe)Leu-(D-Ala)-Arg (Sequence I.D. No. 30) will bias a particular type of β-turn and allow side chain of Leu at position 72 of human C5a to interact with receptors and/or other moieties; and the peptide Tyr-Ser-Phe-Lys-Asp-Met(NMe)Gln-Leu-(D-Ala)-Arg (Sequence I.D. No. 31) will bias a particular type of β-turn and allow side chain of Gln at position 71 of human C5a to interact with receptors and/or other moieites.

Doubly- and triply-methylated peptides may also be utilized to fix the backbone conformation of the analog into a specific β-turn conformation. As for the singly-methylated peptides described above, N-methylation of a residue serves to elongate the backbone conformation of the adjacent, N-terminal residue in a manner similar to the presence of a Pro residue. Unlike a Pro residue, however, N-methylation still affords the contributions made by the side chain of that residue. Such doubly- and triply-methylated peptide analogs include, but are not limited to the following:

Tyr-Ser-Phe-Lys-Asp-Met-Gln-Leu(NMe)D-Ala(NMe) Arg (Sequence I.D. No. 32);

Tyr-Ser-Phe-Lys-Asp-Met-Gln(NMe)Leu-D-Ala(NMe) Arg (Sequence I.D. No. 33);

Tyr-Ser-Phe-Lys-Asp-Met(NMe)Gln-Leu-D-Ala(NMe) Arg (Sequence I.D. No. 34);

Tyr-Ser-Phe-Lys-Asp-Met(NMe)Gln(NMe)Leu-D-Ala-Arg (Sequence I.D. No. 35);

Tyr-Ser-Phe-Lys-Asp-Met-Gln(NMe)Leu(NMe)D-Ala-Arg (Sequence I.D. No. 36); and

Tyr-Ser-Phe-Lys-Asp-Met-Gln(NMe)Leu(NMe)D-Ala (NMe)Arg (Sequence I.D. No. 37)

Synthesis of peptides comprising N-methylated amino acids is described in Example 5.

The C5a analogs of the present invention may be prepared by various synthetic methods of peptide synthesis via condensation of one or more amino acid residues, in accordance with conventional peptide synthesis methods. Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art. When solid-phase synthesis is utilized, the C-terminal amino acid is linked to an insoluble carrier that can produce a detachable bond by reacting with a carboxyl group in a C-terminal amino acid. One preferred insoluble carrier is p-hydroxymethylphenoxymethyl polystyrene (HMP) resin. Other useful resins include, but are not limited to: phenylacetamidomethyl (PAM) resins for synthesis of some N-methyl-containing peptides (this resin is used with the Boc method of solid phase synthesis; and MBHA (p-methylbenzhydrylamine) resins for producing peptides having C-terminal amide groups.

During the course of peptide synthesis, branched chain amino and carboxyl groups may be protected/deprotected as needed, using commonly-known protecting groups. In a preferred embodiment, $N^\alpha$-amino groups are protected with the base-labile 9-fluorenylmethyloxycarbonyl (Fmoc) group or t-butyloxycarbonyl (Boc groups). Side-chain functional groups consistent with Fmoc synthesis are protected as follows: arginine (2,2,5,7,8-pentamethylchroman-6-sulfonyl); asparagine (O-t-butyl ester); cysteine glutamine and histadine (trityl); lysine (t-butyloxycarbonyl); serine and tyrosine (t-butyl). An example of a preferred peptide synthetic method is set forth in Example 1. Modification utilizing alternative protecting groups for peptides and peptide derivatives will be apparent to those of skill in the art.

II. Structural Verification of Peptide Analog Conformations and Assays for Potency and Selectivity It may be desirable to obtain various types of structural verification of the conformational features of C5a analogs of the invention. Such information may be correlated with the biological activity of an analog of interest, for purposes of producing more potent agonists for direct therapeutic use or as high-affinity templates to design C5a antagonists. Such methods, as well as standard biological assays for potency and selectivity are enumerated and described below. These are intended to be illustrative descriptions, and not to limit the invention.

Structural Verification by X-Ray Crystallography.

The conformational flexibility of the C-terminal region of the C5a analogs of the invention has been restricted. For this reason, the analogs may be crystallized under appropriate conditions. Several methods are currently available that may yield crystal suitable for X-ray defraction studies. To test a variety of solvent and precipitant conditions, the hanging drop vapor diffusion method described by Ducruix (1992) may be utilized (A. Ducruix, "Crystallization of Nucleic Acids and Proteins: A Practical Approach", IRL Press. Other systems for screening crystallization conditions are also known in the art (see, e.g., Jancarik & Sung-Hou (1991), J. Appl. Cryst., 24: 409–411), which may be utilized to quickly develop optimum conditions for crystallizing the peptide analogs of the invention. Numerous methods are presently available for generation of high-quality crystals for X-ray diffractions (e.g., dialysis techniques for slowing crystal growth rate after nucleation, thereby promoting the formation of thermodynamically stable crystals, as disclosed by Ducruix, 1992, supra), as well as for data collection and analysis. For example, the combined use of a rotating anode source (e.g., high-density source with copper and silver anodes) with advanced detectors (e.g., imaging-plate area detectors and four-circle goniometers) enables superior crystalographical resolution, due to the lesser time available for crystal degradation during data collection.

Data reduction and analysis can be performed on any of several software packages that are currently commercially available. In a preferred embodiment, analysis of X-ray crystallographical data may be accomplished by the use of the Xtal3.2 package (available from Sydney R. Hall Crystallography Center, University of Western Australia) (Xtal3.2 Reference Manual, Hall, Flack & Stewart, eds., Universities of Western Australia, Geneva and Maryland, 1992). (In an alternative embodiment, graphical visualization of the X-ray crystalographic data may be accomplished through the "insight" software package (Biosym Technologies, San Diego, Calif.).

Peptide Analysis Via NMR Spectrometry.

NMR analysis of C5a peptide analogs may be performed by a variety of techniques known in the art. Preferred embodiments for performing NMR measurements are set forth below.

NMR measurements may be performed on a spectrometer such as the Varian 500 MHz Unity Plus spectrometer. Sequence-specific proton resonance assignments may be obtained from phase-sensitive 2D NOESY spectra (Marion & Wurtich (1983), Biochem. Biophys. Res. Commun., 113: 967). Conformation of initial assignments is accomplished through the comparison of crosspeaks in a NOESY spectrum with those in a total correlation (TOCSY) spectrum acquired for the peptide under similar conditions of temperature and pH, according to standard methods. NOE mixing times are 250 ms and 400 ms at 298° K. and 200 ms at 278° K. Peptides are dissolved in a solution of DMSO:$H_2O$ (2:1), in order to minimize the tumbling rate of the peptide so that NOEs can be observed with normal NOESY techinques. Indeed, the correlation time of $C5a_{65-74}Y65,F67$, $\tau_c$, is calculated to be approximately 4 ns, a value that falls fairly close to the null region ($\tau_c$=0.36 ns) of normal NOESY experiments (Otting et al. (1986), J. Mag. Reson., 66: 187). However, this ratio of co-solvent does not appear to alter the solution structure of the peptide (Neuhaus & Williams (1989), The Nuclear Overhauser Effect, VCH Publishers, New York). A small amount of $D_2O$ (ca. 50 μl) is added for a deuterium lock. Water signal suppression is accomplished by selective irradiation during the relaxation delay and NOE mixing time.

Free induction decay (FID) matrices are acquired in sine modulation along the $\tau_1$ direction (Cantor & Shimmel (1980), Biophysical Chemistry, W. H. Freeman & Co., San Francisco; Bothner-By et al. (1984), J. Amer. Chem. Soc., 106: 811). Fourier transformation and data manipulation the 2D data sets are accomplished according to previously described methods (Carpenter et al. (1994), Protein Science, submitted). Temperature coefficients of the amide proton resonances are determined by regression analysis of the change in NH chemical shifts as a function of temperature. The vicinal coupling constants $^3NH\alpha H$ are obtained directly from finely digitized 1D spectra by measuring peak to peak separation of well-resolved NH-$\alpha H$ doublets. Spectral resolution can be enhanced by Lorenzian-Gaussian apodization when necessary.

Several different techniques may be used for the structural interpretation of the NMR data, utilizing standard distance geometry programs like DGEOM (Blaney et al. (1990), "DGEOM #590": Quantum Chem. Program Exch., Indiana University, Bloomington, Ind.) and/or DSPACE as described previously (Carpenter et al., 1994, supra). Other approaches include the application of the FISINOE or FISINOE-2 program of NMR data analysis, which is described in Example 1.

Determination of Potency and Selectivity in Elicitation of Biological Responses by C5a Analogs.

Numerous biological assays are available for assessing the potency of the C5a analogs of the invention, and their ability to selectively elicit various proinflammatory and immunomodulatory responses. For instance, examples of assays for measuring Class 1 proinflammatory responses include, but are not limited to: (1) smooth muscle contraction assays, using human fetal artery smooth muscle tissue or guinea pig ileum and lung parenchyma (spasmogenic assays, see Example 2); (2) guinea pig platelet aggregation assays (see Example 2); (3) guinea-pig skin permeability assays; and (4) assays for non-neutrophil-mediated changes in vascular permeability in endothelial and epithelial tissues.

Examples of biological assays for assessing Class 2 proinflammatory responses include, but are not limited to: (1) neutrophil polarization (see Example 3); (2) neutrophil degranulation and release of enzymes therefrom (e.g., release of β-glucuronidase, as described in Example 3); and (3) neutrophil chemotaxis (see, e.g., Hugli & Morgan (1984), supra).

Biological assays are also available for measuring immunomodulatory activities of C5a peptide analogs, including release of cytokines and other regulatory factors from leukocytes. Examples of such assays include, but are not limited to: (1) in vitro enhancement of specific antibody responses of human peripheral blood lymphocytes (see Hugli & Morgan, 1984, supra); (2) in vitro bioassay for measuring synthesis and release of cytokines (e.g., IL-1, IL-6, IL-8 and TNF-α) from human monocytes (see, e.g., Morgan et al. (1992), J. Immunol., 148: 3937–3942, describing bioassays for measuring effect of C5a in stimulating IL-6 synthesis and release); (3) enhancement of the cytotoxic T-cell response; and (4) enhancement of the one-way mixed lymphocyte response.

C5a is also known to increase vascular permeability. In the vascular endothelium, C5a produces increases in permeability through either direct effects on the endothelial cells and/or indirect effects requiring the presence of PMNs. The ability of C5a agonist peptides to enhance blood-brain barrier permeability can be evaluated using primary cultured bovine brain microvessel endothelial cells (BBMEC) grown on microporous membrane inserts. Permeability is assessed by measuring the amount of fluorescein-labelled dextran (normally impervious to BBMEC monolayers) that crosses the BBMEC monolayer in the presence of a C5a peptide analog. Functional polarity with respect to the permeability enhancing effects of the C5a peptide agonists is examined by adding the peptides to either the apical (luminal) or basolateral (albuminal) side of the BBMEC monolayers. By analyzing peptides in this system, analogs with selective activity for vascular permeability can be identified. Such C5a peptide agonists are expected to have potential therapeutic benefit for enhancing the delivery of chemotherapeutic agents to the brain. It will be appreciated by those skilled in the art that other methods for assessing the effect of the C5a analogs of the invention on vascular permeability, or on permeability of other cell types, may be used.

It is also advantageous to evaluate the correlation between the ability of a C5a peptide analog to stimulate a specific functional response and the binding affinity of that analog to the C5a receptor expressed on the surface of the responding cell. Thus, binding assays may be utilized to assess peptide analog affinity to C5a receptors on appropriate cells (e.g., human PMN membranes, human monocytes, guinea pig platelets and human endothelial cells). Methods for isolating PMN plasma membranes and for assessing the binding of C5a and C5a peptide analogs to receptors on PMN plasma membranes have been published. See, e.g., English & Anderson (1974), J. Immunol. Meth., 5: 249–252; Rollins et al. (1988), J. Biol. Chem., 263: 520–526. According to the method of Rollins et al. (1988), supra, the displacement of radiolabelled C5a binding to PMN plasma membranes with the selected peptide analogs is measured, and may be analyzed using various software programs (e.g., non-linear curve-fitting program PCNONLIN, available from SCI Software, Lexington, Ky.). In alternative protocols, radiolabelled peptide analogs are bound to PMN plasma membrane, and the ability of non-radiolabelled analogs or natural C5a to displace the radiolabelled analogs is measured. Such PMN binding studies will be useful for determining receptor specificity of the various peptide analogs, if there is any. The procedures described above for binding of C5a and analogs to PMN plasma membranes is adaptable for the examination of binding to plasma membranes from other responsive cell types, such adaptations being within the level of skill in the art.

III. Uses of Potent, Response-Selective C5a Analogs

Immune Adjuvants.

C5a and C-terminal agonist peptides have been shown to stimulate human monocytes to synthesize and release the immune stimulatory cytokines IL-1, IL-6, IL-8 and tumor neucrosis factor-α (TNF-α). C-terminal decapeptide agonists of C5a that select for the C5a receptor on monocytes may be used to stimulate these cells into producing such cytokines without the co-stimulation of other pro-inflammatory cells. Thus, the analogs may be extremely useful as immune adjuvants for the treatment of immune deficiency disorders, as well as for augmenting standard immune therapy for the treatment of cancer, without accompanying inflammatory side effects.

For therapeutic use as immune modulators, the C5a agonists of the invention may be formulated as a pharmaceutical preparation for administration with a biologically acceptable medium such as water, buffered saline, polyol (for example, glycerol, propylene glycol, liquid polyethylene glycol and the like) or suitable mixtures thereof. The C5a agonists of the invention have been found to be active in the sub-micromolar concentration range; hence, concentration of the peptide in the chosen medium should normally be from about 0.05–1.0 mM. As used herein, "biologically acceptable medium" includes any and all solvents, dispersion media and the like which may be appropriate for the desired route of administration of the pharmaceutical preparation. The use of such media for pharmaceutically active substances is known in the art. Except insofar as any conventional media or agent is incompatible with the C5a analogs or other components of a pharmaceutical preparation containing C5a analogs, its use in the pharmaceutical preparation is contemplated. Supplementary active ingredients or other ingredients, such as preservatives and antibiotics, can also be incorporated into the pharmaceutical preparation, if necessary or desirable. It should also be noted that the C5a analogs of the invention described in Examples 1–3 have been shown to be extremely stable toward serum phosphatases (see Example 4) which is a distinct advantage for formulating pharmaceutical preparations.

It is advantageous to formulate the pharmaceutical preparations described above in dosage unit form for ease of administration and uniformity of dosage. Dosage unit form refers to a physically discrete unit of the pharmaceutical preparation, appropriate for the patient undergoing treatment. Procedures for determining the appropriate dosage unit for an immunomodulatory agent are well known to those skilled in the art. The pharmaceutical preparation is preferably administered parenterally, e.g., intravenously or intraperitoneally, in the form of a dosage unit. Other modes of administration may also be effective, such as oral administration.

The pharmaceutical preparation may be administered at appropriate intervals, for example, once a day until the desired immunomodulatory effect has been achieved, after which the dosage may be reduced to a maintenance level. The appropriate intervals in a particular case would normally depend on the condition of the patient. As used herein, the term "patient" includes both humans and animals.

Facilitating Drug Delivery by Increasing Vascular Permeability.

One well-characterized pro-inflammatory response induced by C5a is an increase in vascular permeability that is involved in the recruitment of circulating macrophages and neutrophils from the blood to the surrounding tissue. As described above, C-terminal C5a agonist peptides have also been shown to stimulate increases in permeability of various tissues, such as demonstrated by the guinea-pig skin assay. An increase in vascular permeability can occur when C5a, or an agonist peptide thereof, interacts with neutrophils, thereby stimulating them to synthesize and release a variety of cytokines that induce an increase in permeability in the vascular endothelium.

In addition to neutrophil-mediated effects on vascular permeability, experimental evidence also suggests that C5a has a direct effect on the vascular endothelium, an observation that implies the presence of functional C5a receptors on these cells. C5a peptide analogs of the invention that select for the C5a receptor expressed in these vascular beds can be utilized to increase vascular permeability directly, without engaging circulating neutrophils and the accompanying inflammatory side-effects they induce.

C5a analogs of the invention that directly stimulate vascular tissue to increase permeability can have multiple therapeutic utilities. For example, these analogs could be used to increase permeability across the blood-brain barrier for the purpose of augmenting the delivery of chemotherapeutic agents to the brain for treatment of diseases and disorders of the central nervous system (e.g., Alzheimer's disease and various neurogliomas). As another example, such analogs may be used to increase the vascular permeability of a tumor for the purpose of augmenting delivery of anti-tumor agents, such as monoclonal antibodies that possess specificity for a specific tumor antigen, from the blood to the tumor site. Certain cytokines, such as IL-2 and TNF-α, have been used for this purpose with sucess. C5a peptide analogs could be used alone in the presence of the antibody or the peptide could be covalently attached to the antibody, for site-specific increases in permeability.

The C5a peptide analogs of the invention have been found to elicit specific biological responses in the sub-micromolar range, as described above. Accordingly, dosages of the peptides for use in increasing vascular permeability should be adjusted to deliver concentrations of the peptide in that range at the physiological location where vascular permeability increases are desired. Pharmaceutical preparations comprising appropriate dosages of the C5a peptide analogs of the invention may be formulated as described above.

Anti-Inflammatory Agents.

In accordance with the present invention, conformationally constrained C-terminal C5a peptide analogs have been constructed that approach the full biological potency of natural C5a. For example, one peptide of the invention, Tyr-Ser-Phe-Lys-Asp-Ala-Pro-Leu-(D-Ala)-Arg (Sequence I.D. No. 19) is within 4–5% of full C5a potency, while another Tyr-Ser-Phe-Lys-Pro-Met-Pro-Leu-(D-Ala)-Arg (Sequence I.D. No. 24) is within 20–30% of full C5a potency. These peptides are. believed to be the most potent C5a agonist peptides yet described. It is believed that these potency peptide analogs will be extremely useful as templates for the development of a high-affinity C5a receptor antagonist. Moreover, as the potency of these analogs is increased to a level even more closely approaching that of natural C5a, such high-affinity templates will provide even greater utility. High-affinity C5a receptor antagonists will be therapeutically useful as non-steroidal anti-inflammatory agents. The effective concentrations of such agents should be in the range of that of naturally occurring C5a, i.e., the nanomolar range.

EXAMPLE 1

Conformational Characterization of C-Terminal Peptide Analogs of Human C5a

A series of 24 decapeptide analogs corresponding to the C-terminal region of human C5a ($C5a_{65-74}$) was synthesized with residue substitutions to restrict conformational flexibility in the C-terminus. In this Example, the synthesis and conformational characteristics of the peptide analogs are described.

MATERIALS AND METHODS

Abbreviations.

Except where noted, the single letter designation for the amino acid residues are used: A, alanine; C, cysteine; D, aspartic acid; F, phenylalanine; G, glycine; H, histidine; I, isoleucine; K, lysine; L, leucine; M, methionine; N, asparagine; P, proline; Q, glutamine; R, arginine; S, serine; V, valine; Y, tyrosine. Uppercase letters represent the L-amino acid isomer and lowercase the D-isomer.

Peptide Synthesis, Purification and Characterization.

Peptides were synthesized according to standard solid-phase methodologies on an Applied Biosystems (Foster City, Calif.) Model 430A peptide. synthesizer. Syntheses were performed on a 0.25 mmol scale on p-hydroxymethylphenoxymethyl polystyrene (HMP) resins (0.88 meq/g substitution). $N^\alpha$-amino groups were protected with the base-labile 9-fluorenylmethyloxycarbonyl (Fmoc) group. Side-chain function groups were protected as follows: Arg (Pmc or 2,2,5,7,8-pentamethylchroman-6-sulfonyl); Asp (Ot-butyl ester); Cys, Gln & His (Trt or trityl); Lys (Boc or t-butyloxycarbonyl); Ser & Tyr (t-butyl). Synthesis was initiated by the in situ coupling of the C-terminal residue ($N^\alpha$-Fmoc-L-Arg(Pmc)) to the HMP resin in the presence of excess N-N'-dicyclohexylcarbodiimide (DCC) and 1-hydroxybenzotriazole (HOBT) with 4-dimethylaminopyridine (DMAP) as a coupling catalyst. Peptide chain elongation was accomplished by repetitive Fmoc deprotection in 50% piperidine in NMP followed by residue coupling in the presence of 2-(1H-benzotriazol-1-yl)-1,1,3,3-tetramethyluronium hexafluorophosphate (HBTU).

Disulfide bridge formation was accomplished by oxidation of the di-Cys(SH) peptide in dilute aqueous solution (0.1 mg/ml, pH 7.5) by $K_3Fe(CN)_6$. The course of disulfide formation was monitored by analytical HPLC. The solution was acidified to pH 3.5 and weakly basic cation exchange beads (Amberlite-HCl IRA-68, Sigma) were added to the solution to form a slurry. The slurry was stirred for 20 mins, filtered, and the clear solution frozen and lyophilized.

Side-chain deprotection and cleavage from the resin were achieved in a single step acidolysis reaction by stirring the peptide-resin in a solution of 84t trifluoroacetic acid (TFA), 6t phenol, 2% ethanedithiol, 4% thioanisole, and 4% water for 1.5 hr at room temp. Free peptide was precipitated from this solution by adding cold diethyl ether. The mixture was filtered through a scintered glass Buchner funnel (medium porosity) and the peptide/resin washed twice with cold ether to remove the thiol scavengers. The peptide was extracted by swirling the peptide/resin in the funnel with 20–30 ml aliquots of 10% acetic acid followed by filtration. The extraction aliquots were combined, frozen, and lyophilized to yield the powdered form of the crude peptide.

Peptides were purified by preparative and analytical reverse-phase HPLC on columns packed with $C_{18}$-bonded silica. The details of this procedure have been-described by Ember et al., 1992, supra. All peptides were characterized by amino acid compositional analysis and fast atom bombardment mass spectrometry (FAB-MS). These data are summarized in Table 1.

TABLE 1

Amino Acid Compositional and Mass Spectral Analysis of C5a Analogue Peptides[a]

| Peptide No. | Tyr | Ser | Phe | Lys | Asp | Met | Glx | Leu | Gly | Arg | Other | Mass Spectral Results Theor. | Obs. |
|---|---|---|---|---|---|---|---|---|---|---|---|---|---|
| 1. | | 0.85 (1) | 1.01 (1) | 0.99 (1) | 1.04 (1) | 0.77 (1) | 1.12 (1) | 1.16 (1) | 1.06 (1) | 1.12 (1) | 1.00 (Ile) (1) | 1195 | 1195 |
| 2. | 1.11 (1) | 1.11 (1) | 1.11 (1) | 1.11 (1) | 1.11 (1) | 1.11 (1) | 1.11 (1) | 1.11 (1) | 1.11 (1) | 1.11 (1) | | 1245 | 1245 |
| 3. | 1.05 (1) | 0.86 (1) | 1.04 (1) | 0.93 (1) | 1.07 (1) | 0.96 (1) | 1.07 (1) | 1.04 (1) | | 1.02 (1) | 0.95 (Pro) (1) | 1285 | 1285 |
| 4. | 0.94 (1) | 0.77 (1) | 0.97 (1) | 0.84 (1) | 1.01 (1) | 1.04 (1) | 1.02 (1) | | 0.99 (1) | 0.98 (1) | 1.02 (Pro) (1) | 1228 | 1228 |
| 5. | 1.00 (1) | 0.99 (1) | 0.98 (1) | 1.08 (1) | 1.05 (1) | 0.86 (1) | | 0.99 (1) | 1.00 (1) | 0.99 (1) | 1.07 (Pro) (1) | 1214 | 1214 |
| 6. | ND (1) | ND (1) | ND (1) | ND (1) | ND (1) | ND (1) | | | ND (1) | ND (1) | ND (Pro) (1) | 1198 | 1198 |
| 7. | 1.06 (1) | 0.83 (1) | 1.05 (1) | 0.99 (1) | 1.07 (1) | 0.90 (1) | 0.96 (1) | 1.08 (1) | | 1.03 (1) | 0.99 (Ala) (1) | 1259 | 1259 |
| 8. | 1.02 (1) | 0.96 (1) | 1.03 (1) | 1.00 (1) | 1.26 (1) | 1.00 (1) | 1.05 (1) | 1.00 (1) | | 0.99 (1) | 0.97 (D-Ala) (1) | 1259 | 1259 |
| 9. | 1.03 (1) | 0.97 (1) | 0.98 (1) | 0.89 (1) | 1.09 (1) | 1.02 (1) | 1.04 (1) | 0.96 (1) | 1.06 (1) | 0.97 (1) | | 1245 | 1245 |
| 10. | 1.05 (1) | 0.85 (1) | 1.09 (1) | 1.00 (1) | 0.98 (1) | 0.98 (1) | | 0.93 (1) | | 1.06 (1) | 1.06 (D-Ala), (1) 1.01 (Pro) (1) | 1228 | 1228 |
| 11. | 1.06 (1) | 0.78 (1) | 1.09 (1) | 0.88 (1) | 0.98 (1) | 1.05 (1) | | | 0.92 (1) | 1.11 (1) | 1.10 (Ala), (1) 1.12 (Pro) (1) | 1172 | 1172 |
| 12. | 1.06 (1) | 0.84 (1) | 1.07 (1) | 1.07 (1) | 0.96 (1) | 0.94 (1) | | | | 1.02 (1) | 1.98 (D/L-Ala), (2) 1.03 (Pro) (1) | 1186 | 1186 |
| 13. | 0.92 (1) | 0.71 (1) | 2.06 (1) | 0.99 (1) | 1.00 (1) | 1.01 (1) | | 0.98 (1) | | 1.28 (1) | 1.04 (Pro) (1) | 1304 | ND |
| 14. | 0.98 (1) | 0.94 (1) | 1.06 (1) | 0.95 (1) | 1.06 (1) | 0.99 (1) | | 0.96 (1) | | 0.99 (1) | 2.10 (D/L-Pro) (2) | 1254 | ND |
| 15. | 1.10 (1) | 0.89 (1) | 1.07 (1) | 0.97 (1) | 0.96 (1) | | | 0.94 (1) | 1.00 (1) | 1.01 (1) | 1.04 (Ala), (1) 1.04 (Pro) (1) | 1154 | 1154 |
| 16. | 1.04 (1) | 0.82 (1) | 1.07 (1) | 0.89 (1) | 0.90 (1) | | | 1.04 (1) | 1.12 (1) | 1.08 (1) | 1.01 (Cys), (1) 1.01 (Pro) (1) | 1186 | 1186 |
| 17. | 1.06 (1) | 0.98 (1) | 1.08 (1) | 0.98 (1) | 0.93 (1) | | | 0.91 (1) | | 1.05 (1) | 2.10 (Cys), (2) 1.10 (Pro) (1) | 1232 | 1232 |
| 18. | 1.02 (1) | 0.82 (1) | 1.08 (1) | 1.01 (1) | 0.94 (1) | | | 1.05 (1) | | 1.09 (1) | 1.88 (Cys), (2) 1.11 (Pro) (1) | 1230 | 1230 |
| 19. | 0.97 (1) | 0.80 (1) | 1.06 (1) | 0.95 (1) | 1.04 (1) | | | 1.01 (1) | | 1.04 (1) | 2.05 (D/L-Ala), (2) 1.04 (Pro) (1) | 1168 | ND |
| 20. | 0.95 (1) | 1.05 (1) | 0.96 (1) | 1.09 (1) | | 0.95 (1) | | 1.88 (2) | 1.24 (2) | 1.10 (1) | | 1172 | ND |
| 21. | 0.99 (1) | 0.99 (1) | 1.10 (1) | 1.22 (1) | | | | 2.75 (3) | 1.92 (2) | 1.09 (1) | | 1154 | ND |
| 22. | 1.02 (1) | 0.99 (1) | 1.06 (1) | 1.10 (1) | | 0.99 (1) | | 1.94 (2) | 1.90 (2) | 0.99 (1) | | 1172 | ND |
| 23. | 1.00 (1) | 0.83 (1) | 1.09 (1) | 1.02 (1) | | 0.98 (1) | | 0.93 (1) | 2.19 (2) | 0.94 (1) | 1.00 (Pro) (1) | 1156 | ND |

[a]Values in parentheses are the expected number of residues, numbers directly above them are the observed. ND, not done.

RESULTS AND DISCUSSION

Conformational Characterization. Based on the solution NMR data on human C5a, the tertiary structure for the region 1–63 was derived from the analysis of long- and medium-ranged nuclear Overhauser effects (NOE) (Zuiderweg et al., 1989, supra). For the C-terminal region 64–74, however, long-range NOEs were not observed. Neither were there any observable NOEs between this C-terminal region and other parts of the polypeptide. Moreover, quantitative NOE interpretation was complicated by spectral overlaps. This region of C5a, therefore, was interpreted to be made up of flexible, random structure.

In order to determine the probable backbone conformations within the flexible region of human C5a represented by the C-terminal ten residues ($C5a_{65-74}$), we applied a probabalistic approach (Sherman & Johnson (1993), Prog. Biophys. Molec. Biol., 59: 285–339) that utilized FISINOE-2, a modification of the FISINOE program (Sherman & Johnson (1992), J. Mag. Reson., 96: 457–472). The FISINOE program provides a way to accurately predict protein backbone conformation from NOE data that is, of itself, insufficient to determine accurate structures for proteins in solution. The program combines two types of information to establish protein local structure: the sequential d connectivities (sdc's) derived from NOE data, and a probability density of amino acid residue conformations derived from X-ray structures in the Protein Data Bank (see Bernstein et al., J. Mol. Biol., 80: 319, 1977). The NOE data provides specific information about local structure of the protein or peptide, while the X-ray-derived probability distribution described imperical probabilities for local protein folding. The initial calculations, as described by Sherman et al., J. Biomol. Struct. Dyn., 4: 869 (1987), combined with the experimental demonstrations disclosed by Sherman and Johnson, 1992, supra, show that the combination of NOE data with the $\phi$, $\Psi$ probability distribution is capable of generating an accurate prediction of peptide structure, that exceeds the accuracy of that predicted by NOE data alone.

The FISINOE-2 program, which represents a new version of FISINOE, provides several improvements with respect to predictive accuracy. The new version of the program uses both values of intra-residue and sequential cross-peak intensities, graded as strong, medium and weak, and values of coupling constants' $^3J_{\alpha N}$ and $^3J_{\alpha\beta}$, graded as high, intermediate, low and negligible, as input data to determine the mathematical expectations of the $\phi$, $\psi$ and $\chi_1$ angles and their standard deviations, $\sigma_\phi$, $\sigma_\psi$ and $\sigma_{\chi 1}$. The upper limit for distance when a strong cross peak is observed is set at 2.5 Å, for a medium cross peak—3.0 Å, and for a weak cross peak—3.6 Å. Values of vicinal coupling constants are graded as high (>8 Hz), intermediate (in the interval from 5 to 8 Hz), low (in the interval from 2 to 5 Hz), and negligible (<2 Hz). FISINOE-2 uses joint density distributions of the three angles, $\phi$, $\psi$ and $\chi_1$, for all 20 types of residues. The joint density distributions were obtained on the basis of statistical analysis of Brookhaven Protein Data Bank. FISINOE-2 uses NMR measurements and the joint angular distributions to estimate the upgraded values of the $\phi$, $\psi$ and $\chi_1$ angles and their standard deviations by a Bayesian inferential paradigm. Comprehensive computational experiments made on the basis of simulated NMR data have shown that FISINOE-2 allows the determination of the backbone angles, $\phi$ and $\psi$, with an accuracy of about 20°, and the $\chi_1$ angles—with an accuracy of about 15°. FISINOE-2 also gives stereospecific assignments of β-protons as a by-product of the $\chi_1$ determination.

Input data to the FISINOE-2 program came from the presence and/or absence of sequential d-connectivities from the original $^1$H-NMR data on human C5a (Zuiderweg et al., 1989, supra). The simultaneous presence of sequential $d_{\alpha N}$ and $d_{NN}$ connectivities in the region (64)65–69 as well as $d_{\alpha\beta}$ (i, i+3) was consistent with this region of C5a adopting a helix-like backbone conformation. The region 70–71 was characterized by the presence of $d_{\alpha N}$-connectivities and the absence of $d_{NN}$ connectivities, suggestive of an elongated backbone conformation. The C-terminal end (residues 72–74) was characterized by the presence of $d_{\alpha N}$ and $d_{NN}$ connectivities and by the absence of medium- and long-range NOEs, a pattern consistent with the dynamic averaging of an ensemble of structures with overlapping contributions made by elongated and twisted backbone conformations (see Sherman & Johnson, 1993, supra; Sherman & Johnson, 1992, supra; Wurtrich, in *NMR of Proteins and Nucleic Acids*, John Wiley & Sons, New York (1986), pp.162–175). Thus, the NMR-matched, backbone conformational features of the C-terminal ten-residue region of C5a (C5a$_{65-74}$) can be described as consisting of twisted, helix-like conformation for residues 65–69, elongated conformation for residues 70–71, and flexible structure of overlapping contributions made by twisted and elongated conformations in the C-terminal region 72–74.

It is assumed that the one (or more) biologically active conformation(s) of the C-terminal. decapeptide C5a$_{65-74}$ lies within a low energy ensemble of conformers generated by the sterically allowable range of flexibility within the C-terminal end (residues 72–74). In fact, flexibility in this end of the peptide appears to be important for the expression of biological activity because activity is dramatically affected when this flexibility is restricted (Ember et al., 1992, supra; Sanderson et al., 1993, supra; Taylor et al., 1993, supra). Thus, it is important to identify the conformational features in the C-terminal end of C5a$_{65-74}$ that relate to the expression of various biological activities.

A reverse or β-turn in the C-terminal region of (Gln-71 to Arg-74) of C5a$_{65-74}$ is suggested on the basis of three lines of evidence. The first is the presence of overlapping twisted and elongated structure in this region as determined from our analysis of the NMR data of human C5a. The second is a previously-observed increase in neutrophil membrane binding and chemotactic activity for certain C-terminal octapeptide analogs of C5a in which Gly-73 was substituted with D-Ala (Kawai et al., 1992, supra). This, along with the position of the Gly in the four-residue reverse-turn stretch (i+2, or -Gln-Leu-Gly-Arg), was suggestive of a β-turn that was stabilized by the D-Ala substitution. Indeed, the pattern of changes observed in the biological activity expressed by the conformationally constrained analogs described in Examples 2 and 3 below, not only confirm the presence of a C-terminal, reverse-turn but correlate with a β-turn of type II or V for the Class 1 proinflammatory responses tested (i.e., spasmogenic and platelet aggregatory activities), and a β-turn of the type III' for the Class 2 responses (i.e., neutrophil polarization and enzyme release).

Peptide Characterization.

Table 1 summarizes the amino acid compositional and mass spectral analyses of 23 peptide analogs described herein (peptide 24 was synthesized later). This panel is also listed in Tables 2 and 4, which summarize the biological results in human fetal artery and guinea-pig platelets, and in neutrophils, respectively. Selected peptides are shown in Table 3, which summarizes the results in guinea-pig ileum and lung parenchyma. All peptides were based on the C-terminal 10-residues of human C5a (C5a$_{65-74}$ or ISHKDMQLGR) and on a more potent analog (C5a$_{65-74}$Y65, F67 or YSFKDMQLGR). The replacement of His at position 67 with the aromatic residue Phe (peptide 1, Table 2) has been shown to afford about a 2 order-of-magnitude increase in potency relative to C5a$_{65-74}$ (Mollison et al. (1991), Agent & Actions, Suppl. 35: 17–21; Or et al. (1992), J. Med. Chem., 35: 402–406) Tyr was used in place of Ile-65 in order to provide a site for radioactive iodination for tracer studies (Siciliano et al. (1994), Proc. Natl. Acad. Sci. USA, 91: 1214–1218). In smooth muscle contraction of human fetal artery, C5a$_{65-74}$Y65,F67 was shown to be about 20 times more potent than the C-terminal 19-mer of natural sequence (C5a$_{65-74}$) (FIG. 1, Example 2). Substituted residues that differ from those in C5a$_{65-74}$Y65,F67 are shown in bold face (Tables 2 and 4). All peptides were homogeneous by both analytical RP-HPLC and mass spectral analysis and gave the expected residue molar ratios by compositional analysis and parent ion molecular mass by FAB-MS (see Table 1).

Residue substitutions in C5a$_{65-74}$Y65,F67 were chosen to restrict the flexibility in the C-terminal region of the decapeptide in order to bias certain features of backbone conformation that would be useful in the search for the biologically relevant conformation(s) in the flexible, C-terminal region. Three principal types of modifications were employed. These include (1) Pro substitutions for restricting local $\phi$ angle flexibility and for influencing the allowed conformations of the preproline residue, (2) Ala substitutions for evaluating the contributions made by the side-chains in the peptide, and (3) D-residue substitutions for altering local stereoisomeric arrangements. The changes in biological activity-induced by these restrictions in C-terminal flexibility and conformational space alterations were assessed in spasmogenic assays (smooth muscle contraction in human fetal artery, guinea-pig ileum, guinea-pig lung parenchyma), in guinea-pig platelet aggregation and in neutrophil activation assays (neutrophil polarization and enzyme release), as described in Examples 2 and 3 below.

EXAMPLE 2

Class 1 Proinflammatory Response-Selective Pharmacological Activity of C-Terminal Peptide Analogs of C5a In this Example, we describe the Class 1 proinflammatory response-selective pharmacological activity of the peptide analogs from Example 1.

MATERIALS AND METHODS

Smooth Muscle Contraction Assays.

Tissue strips were suspended in 2 ml organ baths, containing physiological salt solution (Krebs-Ringers solution: 118 mM NaCl, 4.7 mM KCl, 2.5 mM $CaCl_2$, 25 mM $NaHCO_3$, 1.2 mM $KH_2PO_4$, 1.2 mM $MgSO_4$, 10 mM Glucose) maintained at 37° C., pH 7.4 and continuously aerated with a 95% $CO_2$ mixture. Each tissue preparation was equilibrated for 1 hr prior to testing with peptides. All drugs were kept on ice during the procedure and isometric tensions were measured using strain-gauge transducers (Grass FT-03) with a computerized chart recording system (MacLab/8). After the contraction to each peptide reached a plateau, histamine (10 $\mu M$) was added to obtain the maximum tissue response. Because tachyphylaxis occurs rapidly to single doses of C5a or peptides, cumulative dose-response curves could not be obtained. Instead, the dose-response profile was compiled from multiple strips from each tissue. After exposing each strip to a single concentration of the peptide followed by supramaximal histamine, the response was expressed as a percentage of the maximal contraction to histamine. Full dose-response curves for C5a (human recombinant C5a; Sigma) or individual peptides were performed in each experiment for each tissue and the $EC_{50}$ values (i.e., concentration of peptide producing 50t of the maximal response to each peptide) obtained by probit analysis. pD2 transforms [$-\log EC_{50}$ (M)] were calculated for each dose-response curve, and means ±SE obtained for each peptide.

Human Fetal Artery.

Human umbilical cords were obtained from the Mater Misericordiae Hospital, South Brisbane, Queensland within minutes of delivery. The mid-section of the umbilical cord was cut from the placenta, placed in physiological salt solution and stored at 5° C. for up to 24 hrs. This period of storage did not affect the responsiveness of the tissue to drugs. The fetal arteries were dissected out and cut into longitudinal strips. The intimal surface of the arteries was rubbed with a cotton bud to remove the endothelium. Strips approximately 2 cm×3 mm were suspended in organ baths under 20 mN of resting tension. Arterial strips were tested repeatedly with peptides following a 60 min drug-free period of rest between assays (Taylor et al. (1994), Inflammation, in press).

Guinea-Pig Ileum and Lung Parenchyma.

Guinea pigs (250–500 g) of either sex were killed by stunning and exsanguination. The tissues were rapidly removed and placed into chilled (5° C.) physiological salt solutions. Longitudinal strips from the terminal ileum, approximately 2 cm in length, were set up in organ baths with a resting tension of 20 mN. Atropine (0.1 $\mu M$) was added to the ileal preparations to reduce spontaneous activity. Lung parenchymal strips were cut from the peripheral edge of the lungs. These strips (1–2 cm×3–4 mm) were set up with a resting tension of 10 mN. Each ileal and parenchymal strip was tested with peptides one time only.

Platelet Aggregation Assay.

This assay was performed on platelets obtained from the arterial blood of anesthetized male Hartley guinea pigs according to previously published methods (Ember et al., 1992, supra). Briefly, platelet-rich plasma was prepared and diluted to $3\times10^8$ platelets/ml in 0.39% sodium citrate solution. Peptide samples were diluted in a stepwise fashion in 1.5-fold dilutions and placed in 96-well microplates. A 20 ml peptide sample, 80 ml of platelet-rich plasma, and one 3 mm glass bead were placed in each well. The plates were shaken horizontally at 100 rpm for 5 min at 37° C. Platelet aggregation was evaluated visually in an inverted microscope at 40× magnification. The greatest dilution of peptide producing visible aggregation was scored as the threshold concentration for activity. Natural C5a and C3a were included as internal standards. At least three independent duplicate determinations were conducted for every peptide.

RESULTS AND DISCUSSION

Pharmacological Activity.

Table 2 summarizes the pharmacological activities of human C5a, $C5a_{65-74}Y65,F67$, and its analogs in the smooth muscle contraction of human fetal artery and the aggregation of guinea-pig platelets.

TABLE 2

Pharmacological Activities of C5a Analogs in Human Fetal Artery and Guinea-Pig Platelet Aggregation Assays

| Sequence I. D. No. | Peptide | Fetal Artery pD2 ± SE (n)[a] | | $EC_{50}$ $(\mu M)$[b] | Platelet Aggreg $(\mu M)$[c] |
|---|---|---|---|---|---|
| | C5a | 7.92 ± 0.09 | (23) | 0.018 | 0.023 |
| 1 | ISFKDMQLGR | — | | — | 86.3 |
| 2 | YSFKDMQLGR | 5.05 ± 0.06 | (26) | 11.2 | 22.9 |
| 3 | YSFKDMQLPR | <3 | (3) | >1000 | 225 |
| 4 | YSFKDMQPGR | 4.40 ± 0.16 | (4) | 48.0 | 500 |
| 5 | YSFKDMPLGR | 6.18 ± 0.11 | (20) | 1.13 | 6.3 |
| 6 | YSFKDMPPGR | 4.68 ± 0.17 | (4) | 25.1 | 80 |
| 7 | YSFKDMQLAR | 4.04 ± 0.12 | (11) | 122 | 34 |
| 8 | YSFKDMQLaR | 5.42 ± 0.36 | (7) | 12.2 | 20 |
| 9 | YSFKDMQIGR | 3.77 ± 0.39 | (3) | 286 | 150 |
| 10 | YSFKDMPLaR | 6.57 ± 0.08 | (16) | 0.35 | 1.3 |
| 11 | YSFKDMPAGR | <3 | (3) | >1000 | 101 |
| 12 | YSFKDMPAaR | 4.86 ± 0.14 | (6) | 17.9 | 90 |
| 13 | YSFKDMPLfR | 4.53 ± 0.34 | (4) | 51.1 | 2.3 |
| 14 | YSFKDMPLpR | 5.57 ± 0.22 | (4) | 3.70 | 2.7 |
| 15 | YSFKDAPLGR | 6.11 ± 0.15 | (12) | 1.74 | 7.4 |
| 16 | YSFKDCPLGR | 5.79 ± 0.16 | (6) | 2.04 | 2.3 |
| 17 | YSFKDCPLCR | 4.67 ± 0.14 | (8) | 26.6 | 4.1 |
| 18 | YSFKDCPLCR | <4 | (3) | 162 | >410 |
| 19 | YSFKDAPLaR | 6.57 ± 0.15 | (4) | 0.33 | 0.54 |
| 20 | YSFKGMLLGR | 5.34 ± 0.10 | (4) | 4.9 | 10.5 |
| 21 | YSFKGLLLGR | 5.21 ± 0.19 | (2) | 6.6 | 21 |
| 22 | YSFKGMLLGr | 4.43 ± 0.11 | (4) | 40.0 | — |
| 23 | YSFKGMPLGR | 6.23 ± 0.11 | (4) | 0.59 | 6.3 |
| 24 | YSFKPMQLaR | (see text) | | | |

[a]- Mean pD2 ± SE values shown. (n) - number of experiments.
[b]- Mean $EC_{50}$ values derived from individual experiments.
[c]- The dilution of a peptide producing visible platelet aggregation (i.e., threshold response). Peptide substitutions to peptide 2 shown in boldface.

Table 3 summarizes the smooth muscle contractile responses of C5a and selected analogs in guinea-pig ileum and guinea-pig lung parenchyma.

TABLE 3

Pharmacological Activities of C5a Analogs in Guinea-Pig Ileum and Lung Parenchyma

| Sequence I. D. No. | Peptide | Ileum | | Lung Parenchyma | |
|---|---|---|---|---|---|
| | | pD2 ± SE (n)[a] | $EC_{50}$ $(\mu M)$[b] | pD2 (n)[a] | $EC_{50}$ $(\mu M)$[b] |
| 2 | YSFKDMQLGR | 4.51 ± 0.09 (9) | 37.5 | 4.56 ± 0.07 (4) | 28.4 |
| 4 | YSFKDMQPGR | 3.64 + 0.24 (4) | 344 | | |
| 5 | YSFKDMPLGR | 5.14 ± 0.19 (7) | 11.5 | 5.15 ± 0.14 (4) | 8.1 |
| 15 | YSFKDAPLGR | 4.79 ± 0.26 (4) | 26.6 | | |

TABLE 3-continued

Pharmacological Activities of C5a Analogs
in Guinea-Pig Ileum and Lung Parenchyma

| Sequence I. D. No. | Peptide | Ileum pD2 ± SE (n)[a] | Ileum EC$_{50}$ ($\mu$M)[b] | Lung Parenchyma pD2 (n)[a] | Lung Parenchyma EC$_{50}$ ($\mu$M)[b] |
|---|---|---|---|---|---|
| 20 | YSFKGMLLGR | 4.61 ± 0.18 (2) | 26.8 | 5.00 ± 0.24 (4) | 15.1 |
| 21 | YSFKGLLLGR | 4.74 ± 0.02 (2) | 18.1 | 4.70 ± 0.20 (2) | 22.1 |

[a]- Mean pD2 ± SE values shown. (n) - number of experiments.
[b]- Arithmetic mean EC$_{50}$ values derived from average of individual experiments.
Peptide substitutions to peptide 2 shown in boldface.

All analogs screened in these spasmogenic assays induced responses in a dose-dependent manner (see FIG. 1, for example) and were shown to be full agonists compared to natural C5a in these activities. Those peptides of very low potency (EC$_{50}$>1 mM), for which EC$_{50}$ values could not be accurately obtained, were tested for antagonist activity against C5a at concentrations below those that caused contraction or aggregation, but were without effect.

The spasmogenic effects of C5a are due to the release of secondary mediators such as histamine and eicosanoids from inflammatory cells. In guinea-pig ileum, the major contractile mediator is histamine released from degranulating mast cells (Bodammer & Vogt (1970), Int. Arch. Allergy, 39: 648–657; Taylor et al., 1994, supra). In human fetal artery and guinea-pig lung parenchyma, cyclo-oxygenase metabolites mediate the contractile response, which is blocked by cyclo-oxygenase inhibitors (Marceau et al. (1990), Circ. Res., 67: 1059–1070; Stimler et al. (1981), J. Immunol., 126: 2258–2261). Cyclo-oxygenase inhibitors also block the contractile response of the decapeptide analogs of C5a$_{65-74}$Y65, F67 in these tissues (data not shown), although the cell types involved in these latter tissues have not been identified. Mast cells are not present in human fetal artery, but there is some evidence that macrophages may be the cellular source of the eicosanoids released in this tissue (Marceau et al., 1990, supra).

As shown in Table 2, restricting backbone flexibility at position 73 by substituting Pro at this position (peptide 3) was detrimental to spasmogenic and aggregatory activities compared to C5a$_{65-74}$Y65,F67 (peptide 2). The same restriction at the adjacent position, Leu-72 (peptide 4) was also depressive to spasmogenic activity and platelet aggregation (Tables 2 and 3). These observations suggest that the topographic contribution made by the side-chain of Leu-72 and/or the presence of some freedom of backbone flexibility at or near this position is important for the expression of biological activity.

Interestingly, a Pro substitution for Gln at position 71 (peptide 5) afforded a significant (4- to 10-fold) increase in potency in spasmogenic and aggregatory activities relative to peptide 2 (Tables 2 and 3). This suggests that the side-chain of Gln is probably less influential in contributing to a biologically favorable topography and that more favorable topochemical/conformational features appear to result from restrictions in backbone flexibility at this position. This notion was supported by double Pro substitutions in peptide 6. In this case, the decrease in potency observed by the presence of Pro at position 72, which was shown to adversely affect activity (see peptide 4), appeared to be offset by the presence of Pro at the more favorable position 71. The presence of the two Pro residues was not nearly as detrimental to biological activity as was the presence of the single Pro substitution for Leu at position 72 (peptide 4).

Modulating flexibility by increasing steric bulk via an Ala substitution for Gly at position 73 (peptide 7) had an adverse effect on spasmogenic and aggregatory activities compared to peptide 2. However, activity in both assays was completely restored to the level of peptide 2 when Ala-73 was replaced by D-Ala (peptide 8). Moreover, the presence of both D-Ala-73 and Pro-71 appeared to have an additive or complementary effect on activity. Indeed, peptide 10 was about 32-fold more potent than peptide 2 in spasmogenic activity and about 18-fold more potent in platelet aggregation. The peptide having both D-ala-73 and Pro-71 (peptide 10) was substantially more potent than peptides that possessed either substitution alone (peptides 5 and 8). It also appeared that the size of the D-residue side-chain at position 73 was important. The substitution of a bulky D-Phe at position 73 (peptide 13) had an adverse effect on spasmogenic activity, but appeared to benefit platelet aggregation. However, the substitution of a D-Pro at position 73 (peptide 14) had less of a detrimental effect on activity than did D-Phe at this position, but was not as beneficial as when D-Ala occupied position 73 (peptide 10). It is not clear whether this is the exclusive result of the presence of a D-residue at position 73 that lacks a bulky side-chain or whether the presence of Pro at the more critical position 71 overrides any detrimental effects of having D-Pro at position 73 alone.

Unlike the favorable topochemical effect of D-Ala at position 73 (peptide 8), the replacement of Leu-72 with D-Leu (peptide 9) had an adverse effect on spasmogenic and aggregatory activities. These results were similar to that observed with peptide 4 in which Pro was substituted for Leu-72. Even in the presence of the highly favorable substitution of Pro-71, a relatively isosteric substitution of Ala for Leu-72 (peptide 11) was detrimental to activity. However, some recovery was observed when D-Ala occupies position 73 (peptide 12). These results point to the importance of the contribution made by the side-chain of Leu-72 to the expression of a biologically favorable topography. Thus, the integrity of the side chain of Leu at position 72, a backbone restriction at position 71(Pro), and the presence of D-Ala at position 73 seems to confer particularly favorable, C-terminal topochemical features well suited to the potent expression of spasmogenic and platelet aggregatory activities.

Recent NMR results on C5a$_{65-74}$Y65,F67 (peptide 2) suggested that the alkyl side-chain of Met-70 forms a hydrophobic cluster with the aromatic side-chains of Tyr-65 and Phe-67 to stabilize a helical turn in the N-terminal region of the peptide (data not shown). However, shortening the alkyl side-chain of Met-70 and diminishing its hydrophobic character by substituting either Ala (peptide 15) or Cys (peptide 16) had very little effect on activity compared to their homolog, peptide 5 (see also Table 3). The presence of Cys at position 73 in place of Gly (peptide 17), however, seemed to have a more substantial effect on decreasing spasmogenic potency, but not to the extent observed when the isostere Ala occupies this position (peptide 7). The formation of an extended disulfide bridge (peptide 18) that spans the flexible C-terminal region diminished biological potency well beyond that observed with the two reduced Cys present (peptide 17), implying that more global restrictions in flexibility might be less conducive to expressing a biologically favorable topography. These results suggest that the side-chain of Met-70 probably plays a fairly minor role in contributing to the biologically favorable topography within the C-terminal region.

The biological correlations between spasmogenic and platelet aggregatory activities (FIGS. 4-6) suggest that a pharmacologically favorable backbone conformation/ topography within the C-terminal region of $C5a_{65-74}Y65$, F67 can be obtained by D-Ala substitution at position 73, maintaining the integrity of the side-chain of Leu at position 72, and Pro substitution at position 71 for backbone restrictions of flexibility at this site. Also, position 70 (Met) appears to provide a site that affords some leeway in the type of side-chain one chooses to incorporate. This affords an interesting synthetic advantage, since it is now possible to substitute a non-oxidizable residue, Ala (peptide 15) at this position with no demonstrable effects on biological activity. The above biological results also imply that the simplest sequence within the flexible, signal transducing C-terminal region of $C5as_{65-74}Y65,F67$ responsible for optimal expression of activity in these assays would be [YSFKD]APLaR. In fact, this analog (peptide 19) was equipotent to peptide 10 in its spasmogenic activity and about twice as potent in platelet aggregation.

Remarkably, peptide 24 (YSFKPMQLaR) was extremely potent in the smooth muscle contraction assay, exhibiting a spasmogenic activity within 20–30t that of natural C5a. The presence of Pro at position 69 would elongate backbone conformation of the pre-proline residue (Lys-68). These results support the notion that this region of the peptide is in an extended/elongated conformation, rather than in the helix-like conformation proposed earlier. In any case, it appears that the signal-transducing, C-terminal β-turn must extend away from the N-terminal receptor binding region of the peptide.

Peptides 20–23 are rat decapeptide homologs of peptides 2 and 5. The C-terminal octapeptide sequence of rat C5a is known (Kawai et al., 1992, supra) and, as shown in Table 2, the rat decapeptide homolog of peptide 2 (i.e., peptide 20) is about two times more potent in human fetal artery and guinea-pig platelet assays. The oxidizable Met at position 70 was substituted with Leu (peptide 21) with no significant changes in the spasmogenic assays and a slight decrease in platelet aggregation compared to peptide 20. Peptide 22 was substituted with a D-Arg at position 74 to assess the possibilities of this analog acting as an antagonist to natural C5a (see Drapeu et al., 1993, supra). Peptide 22 remained a full agonist of diminished potency, but was devoid of any antagonistic activity. Finally, peptide 23 is the rat homolog of peptide 5. As with peptide 5, the presence of Pro at position 71 seemed to bias a favorable backbone conformation, which was reflected in an increase in potency in fetal artery and platelet aggregation assays compared to peptide 20.

Analysis of Structure-Function Relationships.

As described above, our analysis of the sequential d-connectivities of the C-terminal 10 residues of natural C5a ($C5a_{65-74}$) was consistent with a helix-like structure dominating residues 65/66–69 and an elongated backbone conformation for residues 70–71. On the basis of other lines of evidence, we proposed that the C-terminal residues 72–74 likely exist in a β-turn-like motif, but inherent flexibility in this region precluded the accurate assignment of a specific type of β-turn. In this study, we looked at the biological activities of a panel of peptides in which the flexibility of this C-terminal region has been restricted.

Figure 2:
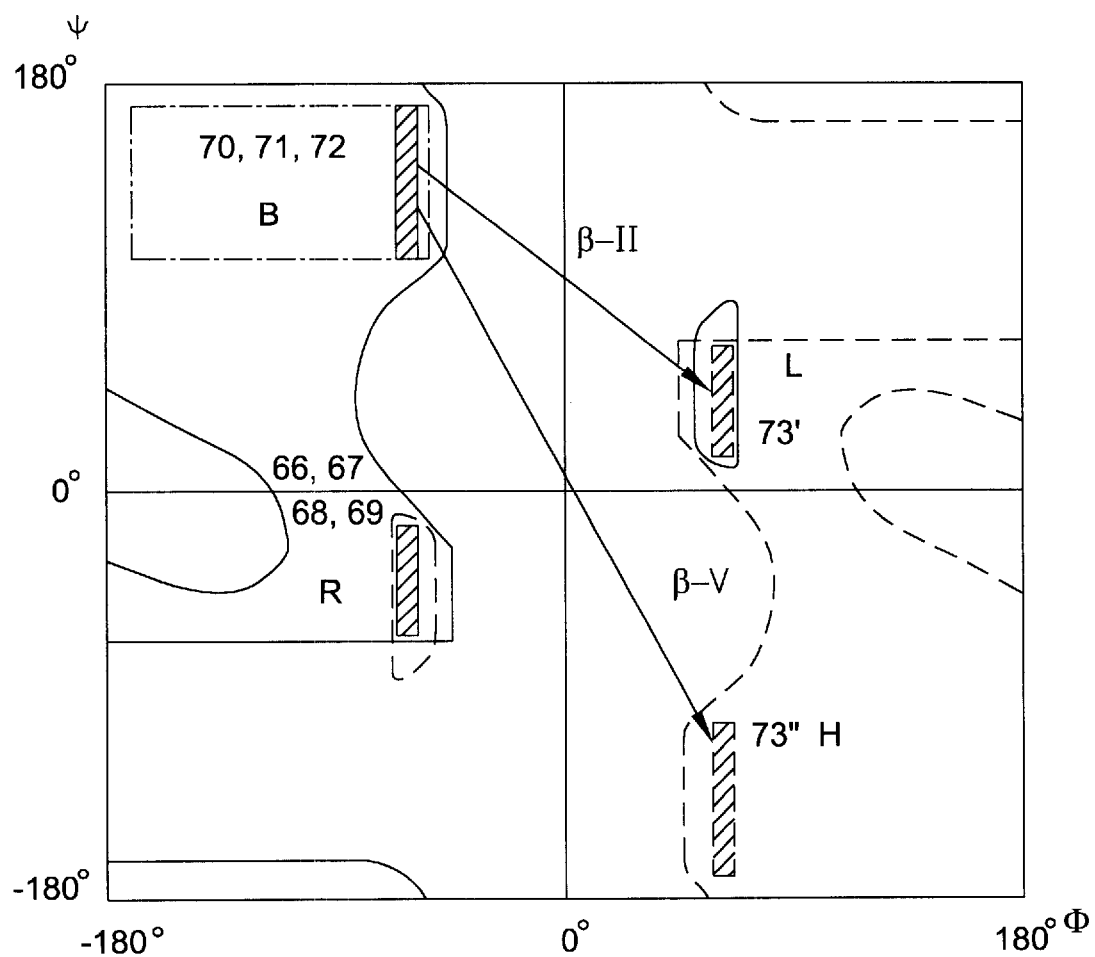

Analysis of the NMR data published for human C5a by the FISINOE-2 program suggested that the decapeptide $C5a_{65-74}$ has helix-like conformation for the region comprised by residues 65/66–69, placing these residues in the region of allowed Ramachandran space at or near $\phi=-90$ and $\Psi=0°$ within the B/R region (FIG. 2). The elongated backbone conformation suggested for residues 70–71 would place them in the B quadrant ($\phi=-90°$ to $-120°$, $\Psi=100°$ to $140°$).

The incorporation of a Pro residue significantly narrows the range of sterically allowed backbone conformations of the preceding (preproline) residue (see Hruby & Nikoforovich, in *Molecular Conformation and Biological Interactions*, P. Balaram & S. Ramasehan, eds., Indian Acad. Sci., Bangalore (1991), pp. 429–445). Thus, a Pro substitution will fix the preproline residue in an elongated conformation by restricting $\Psi$ angle rotations within the narrow interval of about 100° to 160° (i.e., the boxed region within the B quadrant of FIG. 2). Therefore, our assignment of Met-70 to the boxed region of the B quadrant, indicative of elongated conformation, was based on the large increase in potency observed with peptide 5 in which Gln-71 was substituted with Pro. Pro-71 appeared to fix the preproline residue (Met-70) into a biologically favorable elongated conformation.

Our assignment of Gln-71 to this same region in Ramachandran space came from the NMR data interpretation (see above) and from the analysis of structure-function relationships for peptides 4, 6 and 11. The presence of Pro at position 72 (peptide 4) dramatically decreased potency. This observation, however, is somewhat deceptive because it was influenced much more by the lack of the important contribution made by the side chain of Leu-72 than by a detrimental effect on the preproline residue (Gln-71) being forced into an elongated conformation by the Pro. Secondly, Peptide 6, because of the side-by-side Pro residues, must necessarily have residues 71 and 72 occupying the boxed (elongated) region of quadrant B in FIG. 2. In fact, peptide 6 exhibited a reasonable recovery of biological activity, arguing in favor of the backbone of Gln-71 being in an elongated conformation when the more dominating influence of the side-chain of Leu-71 is not taken into account. Furthermore, the presence of an Ala at position 72 should disrupt any positive effect the elongation of backbone conformation at position 71 would have on biological activity. In fact, this was observed in peptide 11, where Ala occupies position 72 adjacent to the elongation-inducing Pro at position 71.

Finally, the assignment of residue Leu-72 to the elongated region B in Ramachandran space was based on the enhancement in activity observed with peptide 14, where a D-Pro (already in a favorable stereoisometric conformation as per D-Ala in peptide 8) occupied position 73. This was also supported by the detrimental effect in activity observed when position 73 is occupied by L-Pro (peptide 3).

Our analysis of the NMR data for human C5a and the positive biological effect of D-Ala substitutions for Gly-73, suggested the possibility of a turn-like motif for the region made up of residues QLGR (residues 71–74). The replacement of Gly-73 with L-Ala (peptide 7) and L-Pro (peptide 3) were both detrimental to biological activity and suggested that the biologically favorable conformation at Gly-73 is not likely to be found in regions B or R in the two, left-hand quadrants of Ramachandran space. However, replacement of Gly-73 with D-Ala (peptide 8) and D-Pro (peptide 14) showed an enhancement in activity and argues strongly in favor of the backbone conformation at position 73 occupying either of the two narrow strips (hashed regions) in the L or H quadrants in the right-hand side of Ramachandran space for a biologically favorable conformation. The presence of D-Arg in peptide 22 showed a decrease in spasmogenic activity and argues for the probability of Arg-74 residing in the B or R quarters of Ramachandran space. Thus, backbone conformations of the C-terminal four residues (71, 72, 73 and 74) were assigned to the regions of allowed Ramachandran space corresponding to B, B, (L or H), B/R respectively (see FIG. 2). The dihedral combination of B, B, L, B is has been shown to correspond to a type II β-turn and B, B, H, B to a type V β-turn (Hruby & Nikoforovich, 1991, supra).

Figure 3:
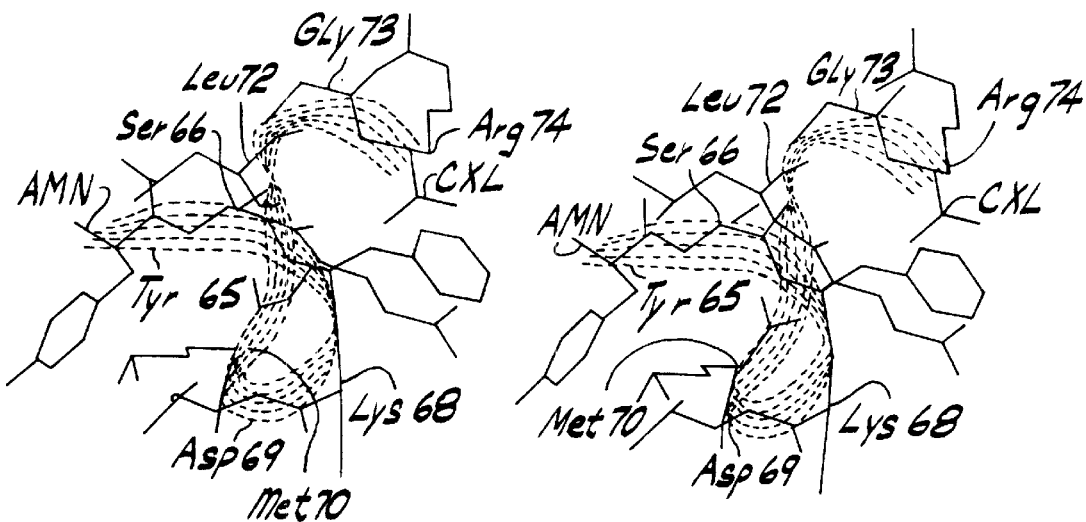

In summary, the backbone conformational features that appear responsible for the expression of spasmogenic and platelet aggregatory activities are: (i) helix-like conformation for residues (65)66-(68)69, (ii) elongated conformation for residues (69)70–71, and (iii) a β-turn of either type II or V for residues (71)72–74. The conformational features are shown in FIG. 3 for the decapeptide agonist $C5a_{65-74}Y65$, F67 (peptide 2).

Pharmacological Analysis.

Figure 4:
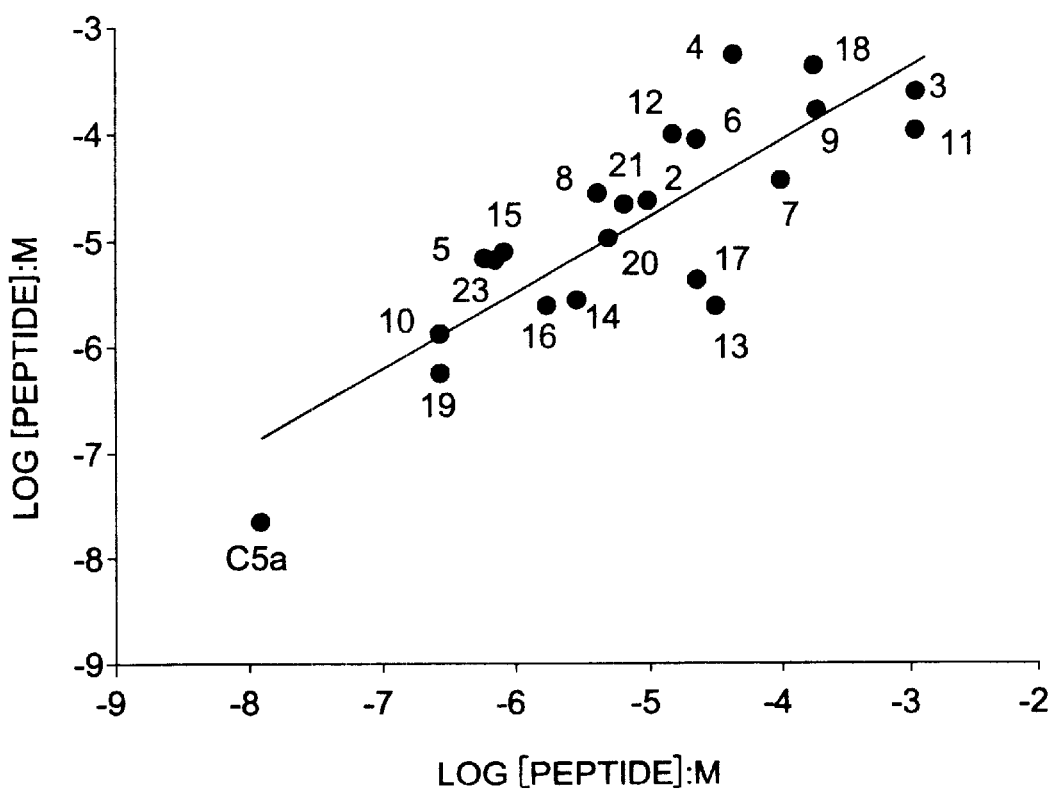
Figure 5:
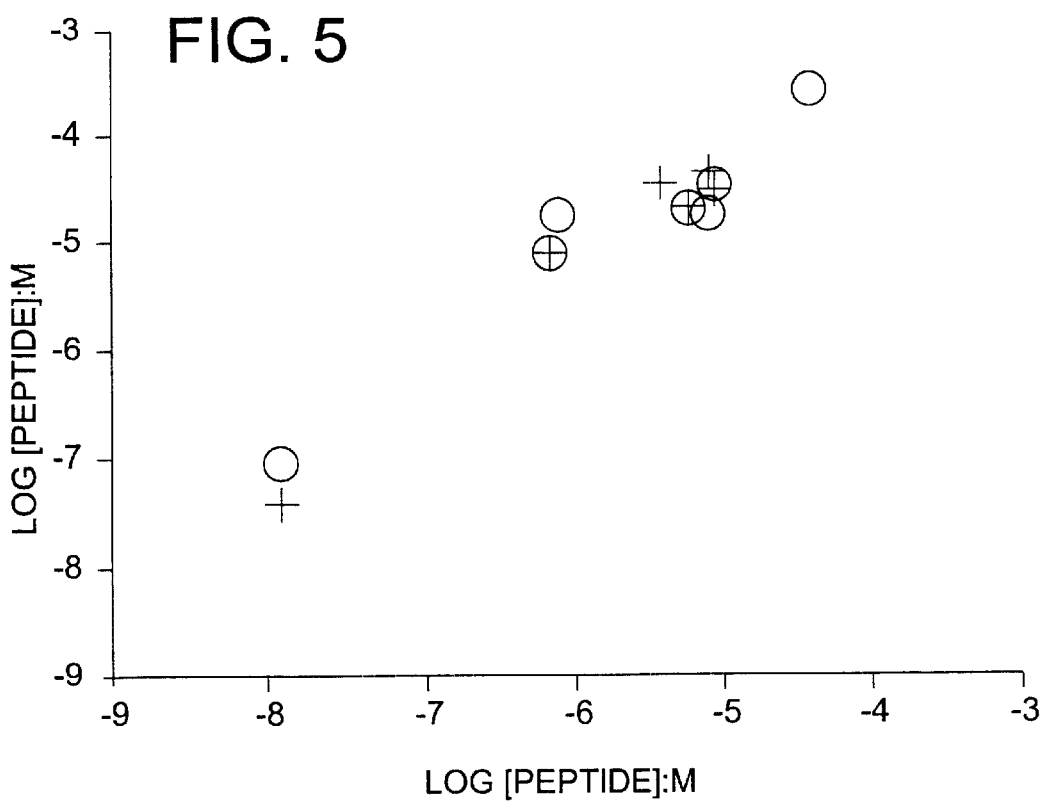
Figure 6:
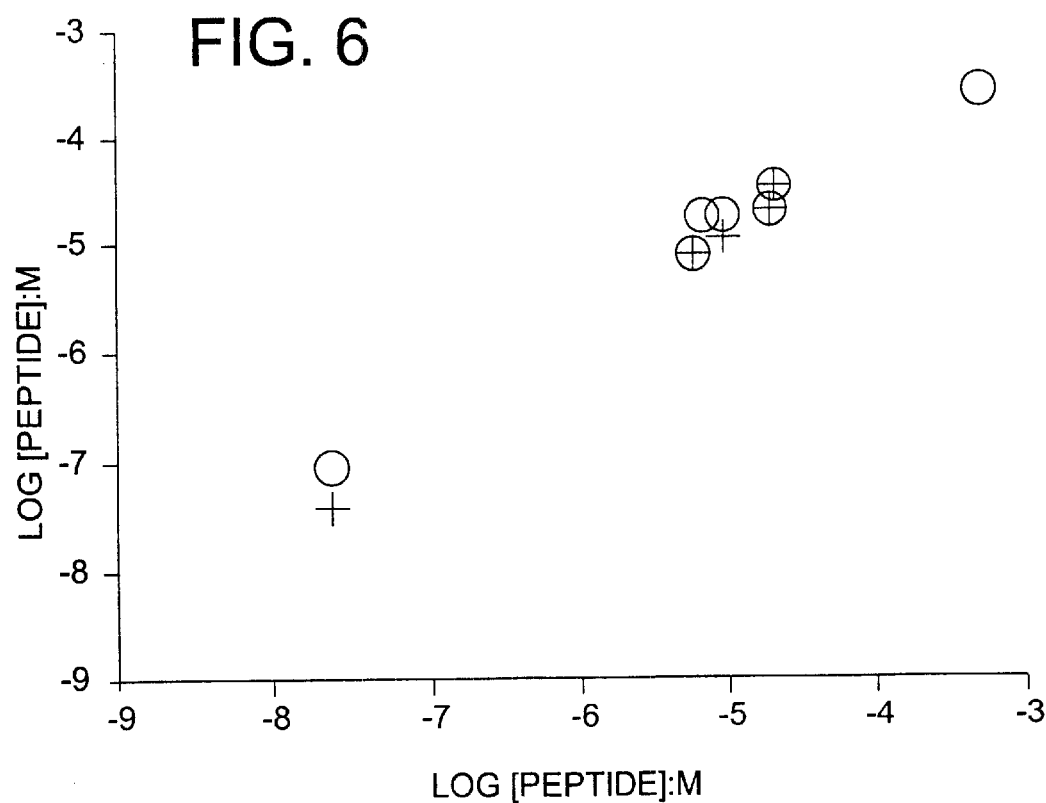

There were significant correlations between $pD_2$ values for human fetal artery and the assays in guinea-pig tissues, as well as with the potencies of analogs in the guinea-pig platelet aggregation assay (FIGS. 4–6). Based on these potency correlations among the different assays used in this study, our biological results did not indicate any ability for this series of conformationally constrained analogs to discriminate between the C5a receptors in the differing tissues. These correlations of peptide potencies between spasmogenic and platelet aggregatory assays also provides evidence that a preferred, common conformational motif exists that subserves these biological activities.

The interaction of C5a with its receptor is thought to involve at least three distinct regions of the ligand (Mollison et al. (1989), Proc. Natl. Acad. Sci. USA, 86: 292–296). However, because our peptides were only a fraction of the size of native C5a (10 vs. 74 residues, respectively) and were probably interacting with one specific region of the C5a receptor (Mollison et al., 1989, supra; Siciliano et al., 1994, supra), we could not infer whether the receptors in the various tissues were the same or different. Thus, no evidence for different C5a receptors in these tissues was suggested by our data. Instead, the observed pharmacological correlations for this series of analogs presented in this paper support the hypothesis of a common C5a receptor recognition site in these tissues.

The combined substitution of Pro-71 with D-Ala-73 resulted in the most potent agonist analogs of the present series, with respect to the Class I biological responses. The relative potencies of peptides in fetal artery were calculated as the log potency ratios at the $EC_{50}$ level compared to C5a. Values were: peptide 2, 2.78±0.10, (0.2% of C5a potency); peptide 5, 2.01±0.12, (1%); peptide 10, 1.42±0.13, (4%) (see also FIG. 1). Our data also indicate that this panel of constrained decapeptide agonists of C5a interact with C5a receptors from certain cell and tissue types and different species in a homogeneous fashion, suggesting that a common conformation motif is involved.

Summary and Conclusions.

In this Example and in Example 1, we have characterized a common, preferred backbone conformation in a series of C-terminal decapeptide agonists of human C5a that correlate with the expression of spasmogenic and platelet aggregatory activities. These structural motifs appear to be a helix-like backbone conformation for residues 65-(68)69, an elongated backbone conformation for residues (69)70–71, and a β-turn of either type II or V for the region (71)72–74. Indeed, peptides that are conformationally biased toward the expression of these backbone features appear particularly potent in these biological assays.

EXAMPLE 3

Class 2 Proinflamatory Response-Selective Pharmacological Activity of C-Terminal Peptide Analogs of C5a: Lack of Correlation with Class 1 Response-Selective Activity In this Example, we describe the Class 2 proinflamatory response-selective pharmacological activity of the peptide analogs from Example 1. The Class 2 and Class 1 response-selective activities of the analogs were compared, and it was determined that little correlation existed between potency in eliciting a Class 1 response and potency in eliciting a Class 2 response.

MATERIALS AND METHODS

Neutrophil Polarization Assays.

Neutrophil polarization assays were conducted as described by Ember et al., 1992, supra. Human neutrophils (PMN) were prepared according to the procedure described by Dahinden et al. (1979), J. Immunol., 130: 857–862. The assay for measuring the effect of C5a analogs on PMN polarization was described by Haston & Shields (1985), J. Immunol. Methods, 81: 229–237. Briefly, PMN ($1 \times 10^6$ cells/ml) were suspended in 10 mM 3- (N-morpholino) propane sulfonic acid (Sigma Chemical Co.) containing EBSS. The cells were incubated with the chemoattractant for 30 minutes at 37° C., then fixed with 2.5% glutraldehyde. After 10 minutes of incubation at room temperature, the cells were washed twice and stored until microscopic examination. Cells deviating from the typical spherical shape were visually scored as polarized. Results are expressed as percent of polarized cells per total cells counted (300 cells counted/sample).

Enzyme Release Assays.

The release of glucuronidase from human neutrophils was determined as described by Schroder et al. (1987), J. Immunol., 139: 3474–3483. Briefly, human neutrophils were pretreated with cytochalasin B (5 µg/ml, 10 min, 37° C.). The cells ($10^6$) were incubated in the presence of stimulants for 60 minutes at 37° C. in a final volume of 200 µl and then centrifuged. The supernatant was collected and 50 µl were incubated with 50 µl of 0.01 M P-nitrophenyl-β-D-glucuronide (in 0.1 M sodium acetate at pH 4 for 18 h) as triplicate determinations in 96-well microtiter plates (Corning). The reaction was stopped by addition of 100 µl of 0.4 M gly buffer at pH 10. The reaction developed color that was read at 405 nm in a Titertec Multiscan (MCC/340) ELISA reader. The β-glucuronidase released was expressed as the percentage of total enzyme in the cell that could be released by addition of 0.2% Triton X-100 (Pierce).

RESULTS AND DISCUSSION

Pharmacological Activity.

Table 4 summarizes the pharmacological activities of human C5a, $C5a_{65-74}Y65$, F67, and its analogs in the polarization of neutrophils and release of β-glucuronidase from neutrophils.

TABLE 4

Pharmacological Activities of C5a Analogs in Polarization of Human Neutrophils and Enzyme Release from Human Neutrophils

| Sequence I.D. No. | Peptide | PMN Polarization EC50 ($\mu M$)[a] | PMN Enzyme Release EC50 ($\mu M$) |
|---|---|---|---|
|  | C5a | 0.0013 | 0.0123 |
| 1 | ISFKDMQLGR | 0.09 | 67.7 |
| 2 | YSFKDMQLGR | 4.0 | 50 |
| 3 | YSFKDMQLPR | 500 | >1000 |
| 4 | YSFKDMQPGR | 22 | 7.0 |
| 5 | YSFKDMPLGR | 5.0 | 80 |
| 6 | YSFKDMPPGR | 50 | 700 |
| 7 | YSFKDMQLAR | 48 | 1000 |
| 8 | YSFKDMQLaR | 1.2 | 32 |
| 9 | YSFKDMQlGR | 3.7 | 520 |
| 10 | YSFKDMPLaR | 2.1 | 57.7 |
| 11 | YSFKDMPAGR | 215 | >1000 |
| 12 | YSFKDMPAaR | 5.6 | >1000 |
| 13 | YSFKDMPLfR | 4.0 | 114 |
| 14 | YSFKDMPLpR | 2.5 | 46.5 |
| 15 | YSFKDAPLGR | 15.8 | 207 |
| 16 | YSFKDCPLGR | 19.5 | >1000 |
| 17 | YSFKDCPLCR | 224 | >1000 |
| 18 | YSFKDCPLCR | 500 | >1000 |
| 19 | YSFKDAPLaR | 2.3 | 114 |
| 20 | YSFKGMLLGR | — | 70 |
| 21 | YSFKGLLLGR | 0.3 | 27.7 |
| 22 | YSFKGMLLGr | — | — |
| 23 | YSFKGMPLGR | 2.0 | 49.6 |

All analogs screened in the neutrophil assays induced response in a dose-dependent manner and were shown to be full agonists compared to natural C5a. Additionally, there was a good end point correlation between the PMN polarization assay results and the enzyme release results, as shown in FIG. 7, which indicates that a common receptor-mediated pathway for both neutrophil-mediated biological responses.

Applying a similar structure-function analysis as described in Example 2 for the spasmogenic and platelet aggregatory activities, it was shown that a change in the conformation of Leu-72 from the B quadrant of the Ramachandran plot to the L quadrant appears to favor the expression of PMN activity (see FIG. 8). This conclusion is supported by the activity observed in PMN polarization in the presence of peptide 9 in which L-Leu-72 was replaced by D-Leu. This substitution and the corresponding slight increase in polarization activity is consistent with Leu-72 existing in the L, H or R quadrants of the Ramachandran plot. Moreover, the strong showing in activity with peptide 14 (in which L-Pro at position 73 is replaced with D-Pro) is consistent with Leu-72 residing in the upper quadrants of Ramachandran (i.e., B or L) because of the influence of D-Pro-73 on the pre-proline residue, Leu-72. Finally, the substitution of Pro for Leu-72 (peptide 4) appears to be much better tolerated in PMN activities than in fetal artery/platelet aggregation, supporting the narrow region of Ramachandran space in the L quadrant (FIG. 8). Thus, it appears that a change in the backbone conformation of Leu-72 from the B quadrant (spasmogenic/aggregatory activities) to the L quadrant favors neutrophil responsiveness.

Accordingly, the backbone conformations of the C-terminal 4 residue (71–74) were assigned to the regions of allowed Ramachandran space corresponding to B, L, (L or H), B/R, respectively. The combination of B, L, L, B is consistent with a type III' β-turn (see Hruby & Nikiforovich, 1991, supra). The combination of B, L, H, B/R corresponds to no known β-turn motif, but may nonetheless represent a basic conformational motif for the C-terminal region.

The correlation in activities for the PMN assays was reminiscent of the similar relationship described above between the activities of these peptides in spasmogenic and platelet aggregatory activities. However, comparative analysis of these data revealed no significant correlations between the PMN assays and the spasmogenic/aggregation assays (see FIG. 9). These initially unexpected results suggest that there is more than one pattern of biological responsiveness toward these peptides. One explanation is that the ability of these peptides to selectively stimulate neutrophil-mediated or spasmogenic responses represents underlying differences in the C5a receptor expressed in these different cells and tissues, and that the conformationally biased peptides described herein can discriminate between those receptors.

EXAMPLE 4

Stability of Peptide Analogs Toward Serum Carboxypeptidases

The loss of the C-terminal Arg residue by the action of serum carboxypeptidases significantly reduces the potency of natural C5a. In fact, C5a des-Arg is thought to be the predominant form of C5a in the serum of humans (see Hugli, 1981, supra). The loss of C-terminal Arg from the decapeptide agonists described in Examples 1–3 above is particularly detrimental to activity. Thus, it is essential to maintain the presence of the C-terminal Arg for the expression of full biological activity and potency. Accordingly, it was necessary to ascertain the stability of the more potent decapeptide agonists toward serum carboxypeptidases, for the purpose of evaluating their potential use in vivo.

FIG. 10 shows HPLC chromatograms for our standard decapeptide agonist YSFKDMQLGR (C5a$_{65-74}$Y65, F67) (FIG. 10A) and the potent spasmogenic/aggregatory analog YSFKDMPLaR (FIG. 10B). Both peptides were incubated in normal human serum at 37° C. for 1 h and thereafter reanalyzed on HPLC. These results indicated significant cleavage of the C-terminal Arg in the standard decapeptide agonist YSFKDMQLGR (FIG. 1A: compare profile "E" with profile "a"), but none in the potent spasmogenic/aggregatory analog YSFKDMPLaR (FIG. 10B: compare profile "d" with profile "a"). From these results, it may be concluded that the conformational constraints placed in the C-terminal end of these peptides generate topographies that are less recognizable by the active sites of serum carboxypeptidases, thereby rendering these constrained peptide analogs more metabolically stable than corresponding flexible analogs.

EXAMPLE 5

Additional Synthetic Schemes for Producing C5a Peptide Analogs

This Example provides information for producing certain preferred peptide analogs of the invention.

a. C5a$_{65-74}$Y65,F67,Aib73 or YSFKDMQLAibR (Sequence I.D. No. 25), where Aib is α-aminoisobutyric acid:

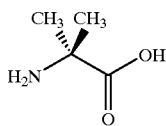

$N^{\alpha}$-Fmoc-Aib can be purchased from Novabiochem, La Jolla, Calif., and coupled to the resin-bound Arg residue in the presence of HBTU/DIEA by standard methods. The rest of the peptide is synthesized by standard Fmoc solid-phase methodologies, purified, and characterized by our previously published procedures (Ember et al., 1992, supra).

The presence of the two methyl groups on the α-carbon of Aib at position 73 will lock the backbone conformation at this position into either the L or R quadrants of Ramachandran space (FIG. 3). The R region of Ramachandran space, however, can be eliminated from consideration because of the increases in spasmogenesis, platelet aggregation and PMN activity observed with peptide 14, YSFKDMPLpR (see Table 3 and FIG. 2), where D-proline occupies only the L-region of Ramachandran space.

Sequence I.D. No. 25 and other sequences described below may be used to advantage to elucidate details of the C-terminal conformation that contributes most to potency and response-selectivity. For example, it can be used for determining whether a type II or a type V β-turn is most favorable for Class response-selectivity. Should YSFKDMQLAibR show an increase in spasmogenic and platelet aggregatory assays, the backbone conformation at position 73 would likely lie within the L region of the Ramachandran plot. Thus, the four C-terminal residues (71–74) would occupy Ramachandran quadrants of B,B,L,B/R; a combination consistent with a β-turn of type II; A decrease in spasmogenic and aggregatory activities would support position 73 residing in the H quadrant of Ramachandran space. This would afford a C-terminal combination of B,B,H,B/R; a combination consistent with a β-turn of type V. Likewise, with respect to Class II response-selectivity, an observed increase in the PMN polarization and/or enzyme activities would support the C-terminal (71–74) combination of B,L,L,B/R; consistent with a β-turn of type III. A decrease in PMN activities would suggest the C-terminal combination of B,L,H,B/R. These two C-terminal conformational possibilities could be further elucidated by additional syntheses, such as those described below.

b. $C5a_{65-74}$Y65,F67,D-Ala73(NMe) or YSFKDMQLa(NMe)R (Sequence I.D. No. 26), where NMe signifies that the amide nitrogen between D-Ala-73 and Arg-74 is methylated:

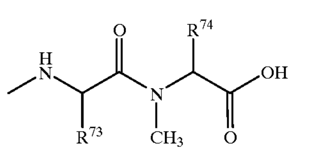

The methyl group on the amide nitrogen behaves similarly to a Pro residue in that it influences the conformation of the adjacent, amino terminal residue (i.e., the pre-methyl residue). Unlike the Pro, however, it does not eliminate the contribution made by the side-chain of the residue at the substituted site in the peptide. The presence of the methylated amide nitrogen between position 73 and 74 will lock the backbone conformation of D-Ala-73 into the L quadrant of the Ramachandran plot only (FIG. 2). Should YSFKDMQLa(NMe)R show an increase in spasmogenic/platelet aggregatory activities, the backbone conformations of the C-terminal four residues (71–74) would be B,B,L,B/R; a combination consistent with a β-turn of type II as the most favorable (between type II and type V) conformation for Class I response-selective activity. A decrease in spasmogenic/aggregatory activity would be more supportive of a B,B,H,B/R combination; consistent with a type V β-turn. Similarly, if an accompanying increase in polarization and/or enzyme release from PMNs is observed, then the C-terminal combination of B,L,L,B/R is favored and, consequently, a β-turn of type III as the best conformation for Class II response-selective activity. A decrease in these PMN activities may support the combination of B,L,H,B/R.

t-Boc-N(Me)Arg(Mts)-OH may be prepared by the N-methylation of Boc-Arg(Mts) with sodium hydride and methyl iodide in dry tetrahydrofuran (THF) according to published methods (McDermott & Benoiton (1973), Can. J. Chem. 51: 1915–1919; Cheung & Benoiton (1977), Can. J. Chem. 55: 906–910). This compound will serve as the C-terminal residue and is attached to a phenylacetamidomethyl (PAM) polystyrene resin according to standard solid phase procedures. The rest of YSFKDMQLa(NMe)R is synthesized by the standard Boc orthogonal strategies. The peptide is cleaved from the resin and deprotected with anhydrous HF. Purification of YSFKDMQLa(NMe)R is accomplished by preparative and analytical HPLC according to our previously published methods (Ember et al., 1992, supra). The peptide may be characterized by amino acid compositional analysis and fast atom bombardment mass spectrometry.

It may also be possible to generate the t-Boc-N(Me)Arg (Mts)-resin directly by methylating Boc-Arg(Mts)-OH already attached to a Merrifield resin by the methylation procedures above. In this case, a Merrifield polystyrene resin is used in order to avoid the potential methylation of the amide nitrogen on the phenylacetaminodomethyl linker used on a PAM resin (see below).

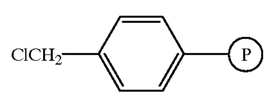

Merrifield Resin

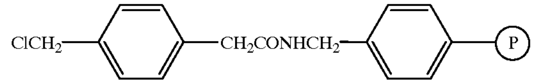

PAM Resin c. C5a65-74Y65,F67,α-MeLeu72,D-Ala73 or YSFKDMQL(α-Me)aR (Sequence I.D. No. 27),-where L(α-Me) is α-methyl Leu:

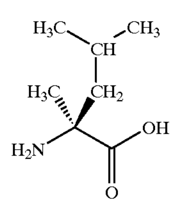

*a*-methyl Leucine

The presence of the methyl group on the α carbon of Leu at position 72 will force backbone conformation at this site into the L quadrant of the Ramachandran plot (FIG. 8). The C-terminal four residues would then correspond to the B,L,L,B/R combination of Ramachandran space, which is consistent with a β-turn of type III'. Thus, a robust increase in PMN activity with YSFKDMQL(α-Me)aR would indicate that a type III' B-turn favors PMN activity, as compared with the alternative favored turn corresponding to B,L,H,B/R. A weak increase or decrease in PMN activity would suggest that the alternative conformation, B,L,H,B/R may be preferred.

The synthesis of $^\alpha$-Boc, α-methylleucine may be performed on a "glycine template" according to the method of Ojima et al. (50). See Scheme 1 below.

contribution made by the side-chains in the C-terminal β-turn region of the C5a analogs. To illustrate, the following analogs can be synthesized and tested in the spasmogenic/platelet aggregatory and PMN assays to elucidate side-chain functionalities that enhance potency and response-selectivity of the C5a analogs: i) YSFKDMQLa(NMe)R (Sequence I.D. No. 28) for fixing the side-chain of D-Ala-73; (ii) YSFKDMQL(NMe)aR (Sequence I.D. No. 29) for fixing the side-chain of Leu-72; iii) YSFKDMQ(NMe)LaR (Sequence I.D. No. 30) for fixing the side-chain of Gln-71; and iv) YSFKDM(NMe)QLaR (Sequence I.D. No. 31) for Scheme 1

The oxazinone 1 is commercially available (Aldrich Chemical Co.) and has been used as a "glycine template" in the asymmetric synthesis of amino acids. The prominent feature of this route is that a quaternary chiral center of desired configuration can be generated by changing the order of addition of the two alkyl halides (i.e., $R^1 \neq R^2$). Once synthesized, the $N^\alpha$-Boc, α-methylleucine is coupled directly to an Boc-Arg(Mts)-PAM resin and the rest of YSFKDMQL(α-Me)aR synthesized using standard Boc solid phase strategies. The peptide is cleaved with anhydrous HF, purified, and characterized by the standard methods. As above, the peptide is tested for its ability to polarize and stimulate enzyme release from human PMNs. An increase in PMN activity would support the notion that a β-turn of type III' is favored for this type of activity.

d. N-Methyl Peptides for Assessing the Importance of the Side-Chain. An interesting advantage that is offered by N-methylated backbone analogs described above is that N-methylation acts similarly to a Pro residue in that it "locks in" a particular backbone conformation of the adjacent, N-terminal residue. However, unlike a Pro residue, the N-methyl group does not eliminate the contribution made by the side-chain moiety at either of the residues adjacent to it. Thus, the N-methyl groups can be used to assess the fixing the side-chain of Met-70. The synthesis of peptide (i) has already been discussed above and the other singly methylated peptides may be synthesized in identical fashion.

Doubly methylated peptides may also be synthesized, such as: i) YSFKDMQL(NMe)a(NMe)R (Sequence I.D. No. 32) for fixing the side-chains of D-Ala-73 and Leu-72; (ii) YSFKDMQ(NMe)La(NMe)R (Sequence I.D. No. 33) for fixing the side-chains of D-Ala-73 and Gln-71; iii) YSFKDM(NMe)QLa(NMe)R (Sequence I.D. No. 34) for fixing the side-chains of D-Ala-73 and Met-70; iv) YSFKDM(NMe)Q(NMe)LaR (Sequence I.D. No. 35) for fixing the side-chains of Met-70 and Gln-71; v) YSFKDMQ(NMe)L(NMe)aR (Sequence I.D. No. 36) for fixing the side-chains of Gln-71 and Leu-72. Finally, the triple methylated peptide YSFKDMQ(NMe)L(NMe)a(NMe)R (Sequence I.D. No. 37) may be synthesized for fixing the side-chains of Gln-71, Leu-72 and D-Ala-73.

In all cases, the individual Boc-N(Me) amino acid are synthesized as described above. The N-methylated residue are then coupled to the growing peptide chain using standard solid phase coupling methods. All methylated peptides are tested in the spasmogenic assays (smooth muscle contraction of human fetal artery and guinea-pig ileum) and guinea-pig platelet aggregatory assays as well as enzyme release from human PMNs and polarization of human PMNs.

The present invention is not limited to the embodiments specifically described and exemplified above, but is capable of variation and modification within the scope of the appended claims.

What is claimed is:

1. A method of increasing permeability of an endothelial or epithelial cell, which comprises contacting the cell with a compound comprising an oligopeptide analog of a C5a carboxy terminus, the analog including a C-terminal segment having a constrained backbone conformation comprising a β-turn, wherein the compound binds to a C5a receptor and possesses a biological activity of a C5a receptor comprising increasing endothelial or epithelial cell permeability, in an amount of the compound effective to increase the permeability of the endothelial or epithelial cell.

2. The method of claim 1, wherein the β-turn is a Type II or Type V β-turn and the activity is a neutrophil non-mediated increases in endothelial or epithelial cell permeability.

3. The method of claim 1, wherein the compound comprises a decapeptide analog of the C5a carboxy terminus, the analog further comprising:

a) an N-terminal segment having a helical backbone conformation; and b) a central segment, disposed between the N-terminal segment and the C-terminal segment, having an elongated backbone conformation.

4. The method of claim 1, wherein the compound comprises the formula:

A1-Ser-Phe-Lys-A2-A3-A4-A5-A6-A7, wherein:

A1 is Tyr, Trp, or N-acetyl derivatives of Tyr or Trp;

A2 is Asp, Gly, Pro or N-methyl derivatives of Asp or Gly;

A3 is Ala, Cys, Met or N-methyl derivatives of Ala, Cys or Met;

A4 is Pro;

A5 is Leu or N-methyl Leu;

A6 is D-Ala, Gly, D-Pro or N-methyl derivatives of D-Ala or Gly; and

A7 is Arg or N-methyl Arg.

5. The method of claim 3, wherein the compound is selected from the group consisting of:

Tyr-Ser-Phe-Lys-Pro-Met-Pro-Leu-(D-Ala)-Arg;

Tyr-Ser-Phe-Lys-Asp-Ala-Pro-Leu-(D-Ala)-Arg;

Tyr-Ser-Phe-Lys-Asp-Met-Pro-Leu-(D-Ala)-Arg;

Tyr-Ser-Phe-Lys-Asp-Met-Pro-Leu-Gly-Arg;

Tyr-Ser-Phe-Lys-Asp-Ala-Pro-Leu-Gly-Arg;

Tyr-Ser-Phe-Lys-Asp-Cys-Pro-Leu-Gly-Arg;

Tyr-Ser-Phe-Lys-Asp-Met-Pro-Leu-(D-Pro)-Arg; and

Tyr-Ser-Phe-Lys-Gly-Met-Pro-Leu-Gly-Arg.

6. The method of claim 1, wherein the endothelial or epithelial cell is a vascular cell.

7. The method of claim 6, wherein the vascular cell is contained within intact vascular tissue, and the compound increases permeability of the vascular tissue.

8. A method of improving vascular delivery of a therapeutic agent, which comprises co-administering to a vascular system the therapeutic agent together with a compound comprising an oligopeptide analog of a C5a carboxy terminus, the analog including a C-terminal segment having a constrained backbone conformation comprising a β-turn, wherein the compound binds to a C5a receptor and possesses a biological activity of a C5a receptor comprising increasing endothelial or epithelial cell permeability, in an amount of the compound effective to increase the permeability of the vascular system.

9. The method of claim 8, wherein the β-turn is a Type II or Type V β-turn and the activity is a neutrophil non-mediated increases in endothelial or epithelial cell permeability.

10. The method of claim 8, wherein the compound comprises a decapeptide analog of the C5a carboxy terminus, the analog further comprising:

a) an N-terminal segment having a helical backbone conformation; and b) a central segment, disposed between the N-terminal segment and the C-terminal segment, having an elongated backbone conformation.

11. The method of claim 7, wherein the compound comprises the formula:

A1-Ser-Phe-Lys-A2-A3-A4-A5-A6-A7, wherein:

A1 is Tyr, Trp, or N-acetyl derivatives of Tyr or Tip;

A2 is Asp, Gly, Pro or N-methyl derivatives of Asp or Gly;

A3 is Ala, Cys, Met or N-methyl derivatives of Ala, Cys or Met;

A4 is Pro;

A5 is Leu or N-methyl Leu;

A6 is D-Ala, Gly, D-Pro or N-methyl derivatives of D-Ala or Gly; and

A7 is Arg or N-methyl Arg.

12. The method of claim 10, wherein the compound is selected from the group consisting of:

Tyr-Ser-Phe-Lys-Pro-Met-Pro-Leu- (D-Ala)-Arg;

Tyr-Ser-Phe-Lys-Asp-Ala-Pro-Leu-(D-Ala)-Arg;

Tyr-Ser-Phe-Lys-Asp-Met-Pro-Leu-(D-Ala)-Arg;

Tyr-Ser-Phe-Lys-Asp-Met-Pro-Leu-Gly-Arg;

Tyr-Ser-Phe-Lys-Asp-Met-Pro-Leu-Gly-Arg;

Tyr-Ser-Phe-Lys-Asp-Cys-Pro-Leu-Gly-Arg;

Tyr-Ser-Phe-Lys-Asp-Met-Pro-Leu-(D-Pro)-Arg; and

Tyr-Ser-Phe-Lys-Gly-Met-Pro-Leu-Gly-Arg.

13. The method of claim 8, wherein the therapeutic agent is a chemotherapeutic agent or an anti-tumor agent.

14. The method of claim 12, wherein the therapeutic agent is an antibody.

* * * * *

UNITED STATES PATENT AND TRADEMARK OFFICE
CERTIFICATE OF CORRECTION

PATENT NO. : 6,465,614 B1
DATED : October 15, 2002
INVENTOR(S) : Sanderson et al.

It is certified that error appears in the above-identified patent and that said Letters Patent is hereby corrected as shown below:

Column 5,
Line 55, reading "a-methyl" should read -- α-methyl --

Column 6,
Line 65, reading "$C5_{65-74}$" should read -- $C5a_{65-74}$ --

Column 20,
Line 48, reading "84t" should read -- 84% --
Line 49, reading "6t phenol" should read -- 6% phenol --

Column 21,
Table 1, the predicted value under Other for Peptide No. 6 reading "(1)" should read -- (2) --

Column 25,
Line 25, reading "50t" should read -- 50% --

Column 29,
Line 18, reading "$C5as_{65-74}$" should read -- $C5a_{65-74}$ --
Line 25, reading "20-30t" should read -- 20-30% --

Column 35,
Line 28, reading "Class" should read -- Class --

UNITED STATES PATENT AND TRADEMARK OFFICE
CERTIFICATE OF CORRECTION

PATENT NO. : 6,465,614 B1
DATED : October 15, 2002
INVENTOR(S) : Sanderson et al.

It is certified that error appears in the above-identified patent and that said Letters Patent is hereby corrected as shown below:

Column 64,
Lines 46 and 47, reading "Tyr-Ser-Phe-Lys-Asp-Met-Pro-Leu-Gly-Arg; Tyr-Ser-Phe-Lys-Asp-Met-Pro-Leu-Gly-Arg;" should read
-- Tyr-Ser-Phe-Lys-Asp-Met-Pro-Leu-Gly-Arg;
Tyr-Ser-Phe-Lys-Asp-Ala-Pro-Leu-Gly-Arg; --

Signed and Sealed this

Eighteenth Day of March, 2003

JAMES E. ROGAN
*Director of the United States Patent and Trademark Office*